United States Patent
Liang et al.

(10) Patent No.: US 10,899,744 B2
(45) Date of Patent: Jan. 26, 2021

(54) CRYSTALLINE FORM OF COMPOUND SUPPRESSING PROTEIN KINASE ACTIVITY, AND APPLICATION THEREOF

(71) Applicant: XCOVERY HOLDINGS, INC., Palm Beach Gardens, FL (US)

(72) Inventors: Congxin Liang, Palm Beach Gardens, FL (US); Yongbin Ma, Hangzhou (CN); Wei He, Beijing (CN)

(73) Assignee: XCOVERY HOLDINGS, INC., Palm Beach Gardens, FL (US)

( * ) Notice: Subject to any disclaimer, the term of this patent is extended or adjusted under 35 U.S.C. 154(b) by 0 days.

(21) Appl. No.: 16/306,104

(22) PCT Filed: Jun. 1, 2017

(86) PCT No.: PCT/CN2017/086760
§ 371 (c)(1),
(2) Date: Nov. 30, 2018

(87) PCT Pub. No.: WO2017/206924
PCT Pub. Date: Dec. 7, 2017

(65) Prior Publication Data
US 2019/0135792 A1    May 9, 2019

(30) Foreign Application Priority Data

Jun. 1, 2016  (WO) ................ PCT/CN2016/084300

(51) Int. Cl.
| | | |
|---|---|---|
| *A61K 31/506* | (2006.01) | |
| *C07D 403/12* | (2006.01) | |
| *A61K 31/501* | (2006.01) | |
| *A61P 9/00* | (2006.01) | |
| *C07D 403/10* | (2006.01) | |
| *A61P 35/00* | (2006.01) | |
| *A61P 25/00* | (2006.01) | |
| *A61P 3/00* | (2006.01) | |
| *A61K 9/20* | (2006.01) | |
| *A61K 9/48* | (2006.01) | |

(52) U.S. Cl.
CPC .......... *C07D 403/12* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 31/501* (2013.01); *A61P 3/00* (2018.01); *A61P 9/00* (2018.01); *A61P 25/00* (2018.01); *A61P 35/00* (2018.01); *C07D 403/10* (2013.01); *C07B 2200/13* (2013.01)

(58) Field of Classification Search
CPC .............. A61K 31/506; C07D 403/12
USPC .................... 514/252.02; 544/238
See application file for complete search history.

(56) References Cited

FOREIGN PATENT DOCUMENTS

| | | |
|---|---|---|
| CN | 102098917 | 6/2011 |
| CN | 103298806 | 9/2013 |
| RU | 2526618 | 8/2014 |
| WO | WO 2004/076412 | 9/2004 |
| WO | WO 2006/021881 | 3/2006 |
| WO | WO 2006/021886 | 3/2006 |
| WO | WO 2006/076412 | 7/2006 |
| WO | WO 2009/154769 | 12/2009 |
| WO | WO2012/048259 | * 4/2012 ........... C07D 403/12 |
| WO | WO 2012/048259 | 4/2012 |

OTHER PUBLICATIONS

Bastin et. al. Organic Process Research & Development 2000, 4, 427-435.*
Stahl, et. al. Handbook of Pharmaceutical Salts, (2002), 1-374.*
Extended European Search Report issued in corresponding European Application No. 17805869.9, dated Nov. 5, 2019.
Hilfiker et al., "Relevance of Solid-state Properties for Pharmaceutical Products" *Polymorphism: in the Pharmaceutical Industry* 2006, pp. 1-19.
Amato et al., "EPHA2 Blockade Overcomes Acquired Resistance to EGFR Kinase Inhibitors in Lung Cancer" *Cancer Res.*, 2016, 76(2):305-318.
Anastassiadis et al., "Comprehensive assay of kinase catalytic activity reveals features of kinase inhibitor selectivity" *Nat Biotechnol.*, 2011, 29(11):1039-1045.
Bang et al., "Clinical Activity of the Oral ALK Inhibitor PF-02341066 in ALK-positive Patients with Non-small Cell Lung Cancer (NSCLC)" *J. Clin. Oncology*, 2010, 28:7S Suppl, abstr3.

(Continued)

*Primary Examiner* — Jeffrey H Murray
(74) *Attorney, Agent, or Firm* — Norton Rose Fulbright US LLP

(57) ABSTRACT

Provided are a compound as represented by structural formula (I) ({5-[(1R)-1-(2,6-dichloro-3-fluorophenyl)ethoxy]-6-aminopyridazin-3-yl}-N-{4-[((3S,5R)-3,5-di methylpiperazinyl)carbonyl]phenyl}carboxamide hydrochloride) and a novel crystalline form of a hydrate or solvate of the compound. Further provided are a manufacturing method of the compound and crystalline form, a related intermediate, a pharmaceutical composition comprising the compound, an application using the compound or the crystalline form for preparing a pharmaceutical product for treating a disease, symptom, or disorder, and a therapeutic method for treating a disease, symptom, or disorder.

Formula I

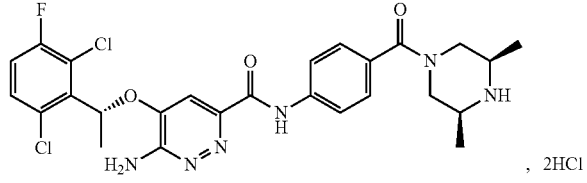

, 2HCl

32 Claims, 6 Drawing Sheets

(56) References Cited

OTHER PUBLICATIONS

Bergethon et al., "ROS1 Rearrangements Define a Unique Molecular Class of Lung Cancers," *Journal of Clinical Oncology*, 2012, 30(8):863-670.

Choi et al., "Identification of Novel Isoforms of the EML4-ALK Transforming Gene in Non-Small Cell Lung Cancer" *Cancer Res.*, 2008, 68(13):4971-4976.

*International Journal of Pathology and Clinical Med.*, 2005, 25(5):441-443 (Translation Not Available).

International Search Report and Written Opinion issued in International Patent Application No. PCT/CN2017/086760, dated Aug. 29, 2017.

Li et al., "Axl as a potential therapeutic target in cancer: role of Axl in tumor growth, metastasis and angiogenesis," *Oncogene*, 2009, 28:3442-3455.

Michieli et al., "Mutant Met-mediated transformation is ligand-dependent and can be inhibited by HGF antagonists" *Oncogene*, 1999, 18:5221-5231.

Pasquale, "Eph receptors and ephrins in cancer: biodirectional signaling and beyond," *Nat Rev Cancer*, 2010, 10:165-180.

Vaishnavi et al., "Oncogenic and drug sensitive NTRK1 rearrangements in lung cancer" *Nature Medicine*, 2013, 19(11):1469-1472.

Webb et al., "Anaplastic lymphoma kinase role in cancer pathogenesis and small-molecule inhibitor development for therapy" *Expert Rev. Anticancer Ther.*, 2009, 9(3):331-356.

Wiesner et al., "Alternative transcription initiation leads to expression of a novel ALK isoform in cancer" *Nature*, 2015, 526:453-457.

"Clinical Pharmacokinetics." *Theoretical, applied and analytical aspects*, edited by V.G. Kukes, Geotar-Media, 2009, 23 pages (English Translation provided).

Berge et al., "Pharmaceutical Salts" *Journal of Pharmaceutical Sciences* 1977, 66(1), pp. 1-19.

Caira, Mino R., "Crystalline Polymorphism of Organic Compounds" *Topics in Current Chemistry* 1998, 198, pp. 163-208.

Morissette et al., "High-throughput crystallization: polymorphs, salts, co-crystals and solvates of pharmaceutical solids" *Advanced Drug Delivery Reviews* 2004, 56, pp. 275-300.

Office Action issued in Corresponding Russian Application No. 2018145183, dated Jun. 16, 2020 (No English translation provided).

\* cited by examiner

CRYSTALLINE FORM OF COMPOUND SUPPRESSING PROTEIN KINASE ACTIVITY, AND APPLICATION THEREOF

CROSS-REFERENCE TO RELATED APPLICATIONS

This application is a national phase under 35 U.S.C. § 371 of International Application No. PCT/CN2017/086760, filed Jun. 1, 2017, which claims priority to International Application No. PCT/CN2016/084300, filed Jun. 1, 2016, entitled "CRYSTALLINE FORM OF COMPOUND SUPPRESSING PROTEIN KINASE ACTIVITY, AND APPLICATION THEREOF", each of which are hereby incorporated by reference in their entirety.

FIELD OF THE INVENTION

The present invention relates to the new crystalline forms of a novel compound {5-[(1R)-1-(2,6-dichloro-3-fluorophenyl) ethoxy]-6-aminopyridazin-3-ly}-N-{4-[((3S,5R)-3,5-dimethylpiperazinyl) carbonyl] phenyl} carboxamide hydrochloride and hydrate or solvate thereof; The present invention further relates to the preparation method of the compound and crystalline forms and related intermediates, pharmaceutical compositions comprising the compound described, and their use in inhibiting the activity of protein kinase (PK). The present invention also relates to a method of using at least one of the above-described compounds or crystalline forms and pharmaceutical compositions for treating a disease, a disorder or a condition associated with modulation of protein kinase.

BACKGROUND OF THE INVENTION

Protein kinases are enzymes that catalyze the phosphorylation of proteins, in most cases, the phosphorylation occurs on the serine (ser), threonine (thr) and tyrosine (tyr) residues of the proteins. Many aspects of cellular life (such as cell growth, differentiation, proliferation, cell cycle and survival) depend on the activity of protein kinases. Moreover, aberrant activity of protein kinase is associated with many disorders such as cancer and inflammation.

More than 500 kinds of protein kinases have been found so far. They can be divided into five categories according to the types of amino acid residues whose substrate proteins are phosphorylated: ①serine/threonine (Ser/Thr) protein kinase: the hydroxyl of the protein is phosphorylated; ②tyrosine (Tyr) protein kinase: the phenolic hydroxyl of protein is served as phosphorus receptor; ③histidine protein kinase: the basic group of histidine, arginine or lysine of protein is phosphorylated; ④tryptophan protein kinase: protein tryptophan residues is served as phosphorus receptor; ⑤aspartyl/glutamyl protein kinase: the acyl group of protein is served as phosphate receptor.

Protein tyrosine kinase (PTK), more than 100 family members been found currently, plays an important role in the regulation of cell differentiation, growth and activation. PTK can be divided into two categories, receptor type and non-receptor type according to their structure, the former known as transmembrane PTK, the latter known as intracellular PTK.

The occurrence and development of human tumors depend on the activation of a series of oncogenes and the inactivation of tumor suppressor genes. In the study of epithelial tumors, it is found that transmembrane protein of Receptor tyrosine kinase (RTKs) plays a fundamental role in the regulation of cell growth, differentiation and survival, and plays a vital role in the occurrence and development of tumors.

The MET proto-oncogene subfamily in RTKs has 2 members, MET and RON (receptor d'origine nantais).

The C-Met proto-oncogene encodes Met receptor tyrosine kinase. Met receptor, a 190 KDa glycosylated dimeric complex, consists of a α chain of 50 KDa that is disulfide linked to a β chain of 145. The α chain is found extracellularly, while the β chain includes the transmembrane and cytoplasmic domain. Met plays a role in tumorigenesis and metastasis, and Met is transformed, tumorigenesis and metastasis with the expression of its ligand hepatocyte growth factor (HGF). (Jefferson, M. et al, Oncogene 1996, 13, 853-856; Michieli, P. et al, Oncogene 1999, 18, 5221-5231). C-Met is overexpressed in a significant percentage of human cancer and amplified during the transition between primary tumors and metastases. Numerous studies have linked the expression of C-Met and/or HGF/SF to cancer progression of different types. In addition, the overexpression of C-Met or HGF has been shown to correlate with poor prognosis and prognosis of disease in a variety of major human cancers (including lung cancer, liver cancer, gastric cancer and breast cancer). C-Met is also directly involved in cancers that have not been successfully treated, such as pancreatic cancer, neuroglioma and hepatocellular carcinoma.

Homologues of RON include Stk (mouse) and Sea (chicken). Its ligand is macrophage stimulating protein (MSP), which is a serum protein, homologous to HGF. RON gene is located on human chromosome 3p21, comprising 20 exons and 19 introns. The mature RON protein is a heterodimer composed of α and β subunits with a molecular weight of about 185 KDa. RON gene product can be detected in a variety of normal human tissues. RON is expressed in human epithelial cells, granulocytes, mononuclear macrophages, megakaryocytes, osteoclasts, tonsillar germinal layer, small intestine, colon, kidney, lung and bone marrow cells. In recent years, studies have shown that in many human primary tumor and tumor cell lines including the digestive system, urinary system, lung and breast, the expression of RON is significantly altered in quality and quantity. The oncogenic activity of RON is correlated with the activity of kinases, and the RON kinase activity can be significantly up-regulated by overexpression, mutation and cleavage mechanisms leading to the malignant transformation, growth and movement of cells. RON can also work alone or in cooperation with other factors to cause tumor invasion and metastasis (International Journal of Pathology and Clinical Medic, 2005, 25(5):441-443).

CSF1R (colony stimulating factor 1 receptor), also known as C-fms, is a single chain transmembrane receptor tyrosine kinase and is a member of the RTKs family that contains immunoglobulin (Ig) motifs. CSF1R is predominantly expressed on cells of monocytic lines as well as cells of the female reproductive tract and placenta. It was also found that the CSF1R is expressed in Langerhans cells, subgroups of smooth muscle cells, B cells and microglia cells in the skin. The main biological effects of CSF1R signal transduction is derived from the differentiation, proliferation, migration and survival of precursor macrophages and osteoclasts in monocyte lines.

Axl belongs to a subfamily of receptor tyrosine kinases that also includes Tyro 3 and Mer. The overexpression of Axl has been reported in many human cancers and is associated with infection and metastasis in lung cancer, prostate cancer, breast cancer, gastric cancer, renal cell carcinoma and glioblastoma. Recent studies have shown that overexpression of Axl via "tyrosine kinase switch" causes imatinib resistance in gastrointestinal stromal tumor. The expression of Axl is induced by chemotherapeutic drugs and the overexpression of Axl leads to resistance in acute myeloid leukemias, suggesting that Axl may be involved in the regulation of various aspects of tumorigenesis. (Oncogene, 2009, 28:3442).

EphA2 belongs to the largest subgroup EPH RTKs of receptor tyrosine kinase, and studies have shown that EphA2 is associated with a series of regulation of pathological conditions, including tumors (Pasquale EB. Eph receptors and ephrins in cancer: bidirectional signaling and beyond. Nat Rev Cancer 2010; 10:165-80). Recently, studies have shown that EphA2 block can overcome the acquired resistance of EGFR kinase inhibitors in lung cancer (Amato et al. Cancer Res 2016; 76(2); 305-18).

ROS1 is a member of the insulin receptor family. Recently, ROS1 rearrangement was found in a small number of patients with lung cancer. And kazolinib, as an inhibitor of ROS1, is very effective in treating these patients (Bergethon et al. J. Clin. Oncol. 2012; 30(8), 863).

NTRK1 rearrangements with tumorigenicity and drug sensitivity are also found in lung cancer (Vaishnavi 1 et al. Nature Medicine 2013; 19(11), 1469). NTRK1 gene encodes a high affinity nerve growth factor receptor (TRKA) protein.

Anaplastic lymphoma kinase (ALK) belongs to the RTKs superfamily. Due to the heterotopic t2 chromosome, oncogenic constitutively active ALK fusion proteins are expressed in anaplastic large cell lymphoma (ALCL) and inflammatory myofibroblastic tumor (IMT). ALK has been considered as a proto oncogene in small propotion of non-small cell lung cancer and neurocytoma recently. (Choi et al, Cancer Res 2008; 68:(13); Webb et al, Expert Rev. Anticancer Ther. 2009; 9(3), 331-356).

Recently, a new isotype of ALK was found to be expressed in 11% of melanomas and sporadic other human cancer types, but not in normal tissues (Wiesner et al. Nature 2015; 526, 453). The new ALK transcript initiates the alternative transcription initiation (ATI) of the intron in the ALK 19, known as ALK$^{ATI}$.

ALK is also involved in nervous system diseases. It has been shown that ALK regulates the functions of frontal cortex and hippocampus in adult brain, and ALK is identified as a new target for psychiatric symptoms (such as schizophrenia, depression and substance (cocaine) addiction).

Crizotinib has been reported as an effective inhibitor of HGF receptor tyrosine kinase (C-Met) and ALK (WO2004076412; WO2006021881; WO2006021886).

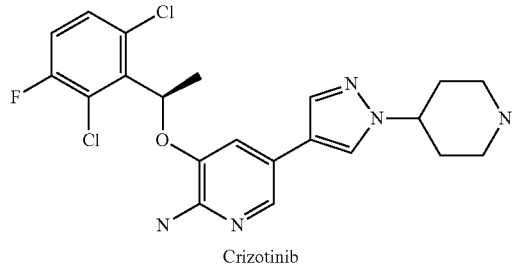 [SMILES: C[C@@H](Oc1cc(-c2cnn(C3CCNCC3)c2)cnc1N)c1c(Cl)ccc(F)c1Cl]

Crizotinib

In Phase I clinical trial of crizotinib, 64% achieved objective response rate (ORR) and 90% achieved disease control (J Clin Oncology 2010; 28: 7S, Suppl; abstr3). Unfortunately, the violent response to crizotinib is only transient. Most patients develop resistance and disease progression after 6-18 months of treatment. In particular, a significant proportion of patients have brain metastases untreated by crizotinib.

The previous patent publications (WO2009/154769A1, WO2012/048259A2, CN103298806B) describe the substituted pyridazine carboxyamide compounds as protein kinase inhibitors, most of which effectively inhibit c-Met and ALK with $IC_{50}$<100 nM. Because there are still unmet needs in the selection of treatment for kinase mediated diseases, we further screen the polymorphic form of substituted pyridazine carboxamide compounds to meet the medical needs of patients.

SUMMARY OF INVENTION

The present invention aims to provide {5-[(1R)-1-(2,6-dichloro-3-fluorophenyl) ethoxy]-6-aminopyridazin-3-ly}-N-{4-[((3S,5R)-3,5-dimethylpiperazinyl) carbonyl] phenyl} carboxamide hydrochloride of Formula I:

Formula I

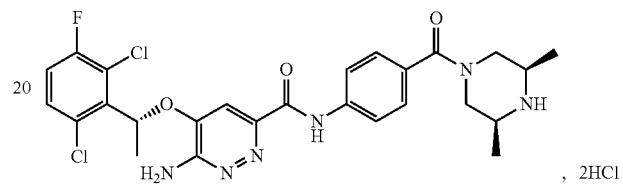

, 2HCl

The invention also relates to a variety of approximately pure crystalline forms of a compound of Formula I, hydrates and/or solvates thereof.

In the present invention, the crystalline forms of the compound of Formula I, hydrates and/or solvates thereof exist in one or more crystalline forms.

The invention first provides a crystalline form of the compound of Formula I, hydrates and/or solvates thereof and its X-ray powder diffraction pattern has characteristic peaks at diffraction angles 2θ of 4.9±0.2°, 10.0±0.2° and 19.3±0.2°. To be convenient, the invention is regarded as Crystalline form A.

Secondly, the present invention further provides preferred embodiments of the above Crystalline form A:

Preferably, the X-ray powder diffraction pattern of the above Crystalline form A has characteristic peaks at diffraction angles 2θ of 4.9±0.2°, 10.0±0.2°, 14.7±0.2°, 16.9±0.2°, 19.3±0.2° and 20.3±0.2°.

Preferably, the X-ray powder diffraction pattern of the Crystalline form A has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2°.

Preferably, the above Crystalline form A has an X-ray powder diffraction pattern approximately as shown in FIG. 1.

The present invention summarizes the X-ray powder diffraction pattern for Crystalline form A as shown in Table 1.

TABLE 1

| 2θ (°) | Intensity (I %) |
|---|---|
| 4.9 ± 0.2 | 13.7 |
| 10.0 ± 0.2 | 100 |
| 14.7 ± 0.2 | 17.7 |
| 16.9 ± 0.2 | 20.3 |
| 19.3 ± 0.2 | 63 |
| 20.3 ± 0.2 | 22.4 |
| 25.5 ± 0.2 | 10.8 |
| 30.7 ± 0.2 | 14.9 |

Preferably, the Crystalline form A has a purity of ≥85%.
Preferably, the Crystalline form A has a purity of ≥95%.
Preferably, the Crystalline form A has a purity of ≥99%.
Preferably, the Crystalline form A has a purity of ≥99.5%.

Preferably, the Crystalline form A is a dihydrate.

The invention further provides another crystalline form of the compound of Formula I, hydrates and/or solvates thereof and its X-ray powder diffraction pattern has the characteristic peaks at diffraction angles 2θ of 10.5±0.2°, 17.4±0.2° and 21.1±0.2°. To be convenient, the invention is regarded as Crystalline form B.

The present invention further provides preferred embodiments of the above Crystalline form B:

Preferably, the X-ray powder diffraction pattern of the above Crystalline form B has characteristic peaks at diffraction angles 2θ of 10.5±0.2°, 17.4±0.2°, 19.7±0.2°, 21.1±0.2°, 23.9±0.2° and 25.5±0.2°.

Preferably, the X-ray powder diffraction pattern of the above Crystalline form B has characteristic peaks at diffraction angles 2θ of 10.5±0.2°, 17.4±0.2°, 19.7±0.2°, 21.1±0.2°, 21.5±0.2°, 23.9±0.2°, 25.2±0.2° and 25.5±0.2°.

Preferably, the above Crystalline form B has an X-ray powder diffraction pattern approximately as shown in FIG. 2.

The present invention summarizes the X-ray powder diffraction pattern for Crystalline form B as shown in Table 2.

TABLE 2

| 2θ (°) | Intensity (I %) |
|---|---|
| 10.5 ± 0.2° | 100 |
| 17.4 ± 0.2° | 56.1 |
| 19.7 ± 0.2° | 26.4 |
| 21.1 ± 0.2° | 33.4 |
| 21.5 ± 0.2° | 23.6 |
| 23.9 ± 0.2° | 26.6 |
| 25.2 ± 0.2° | 25.8 |
| 25.5 ± 0.2° | 28.8 |

Preferably, the Crystalline form B has a purity of ≥85%.
Preferably, the Crystalline form B has a purity of ≥95%.
Preferably, the Crystalline form B has a purity of ≥99%.
Preferably, the Crystalline form B has a purity of ≥99.5%.
Preferably, the Crystalline form B is a trihydrate.

The invention further provides another crystalline form of the compound of Formula I, hydrates and/or solvates thereof and its X-ray powder diffraction pattern has the characteristic peaks at diffraction angles 2θ of 10.2±0.2°, 20.6±0.2° and 21.8±0.2°. To be convenient, the invention is regarded as Crystalline form C.

Secondly, the present invention further provides preferred embodiments of the above Crystalline form C:

Preferably, the X-ray powder diffraction pattern of the above Crystalline form C has the characteristic peaks at diffraction angles 2θ of 10.2±0.2°, 14.7±0.2°, 19.4±0.2°, 20.6±0.2°, 21.8±0.2° and 24.5±0.2°.

Preferably, the X-ray powder diffraction pattern of the above Crystalline form C has the characteristic peaks at diffraction angles 2θ of 8.7±0.2°, 10.2±0.2°, 14.7±0.2°, 19.4±0.2°, 20.6±0.2°, 21.8±0.2°, 24.5±0.2° and 25.9±0.2°.

Preferably, the above Crystalline form C has an X-ray powder diffraction pattern approximately as shown in FIG. 3.

The present invention summarizes the X-ray powder diffraction pattern for Crystalline form C as shown in Table 3.

TABLE 3

| 2θ (°) | Intensity (I %) |
|---|---|
| 8.7 ± 0.2 | 23.1 |
| 10.2 ± 0.2 | 100 |
| 14.7 ± 0.2 | 26.1 |
| 19.4 ± 0.2 | 29.4 |
| 20.6 ± 0.2 | 46.9 |
| 21.8 ± 0.2 | 33.9 |
| 24.5 ± 0.2 | 23.4 |
| 25.9 ± 0.2 | 23.2 |

Preferably, the Crystalline form C has a purity of ≥85%.
Preferably, the Crystalline form C has a purity of ≥95%.
Preferably, the Crystalline form C has a purity of ≥99%.
Preferably, the Crystalline form C has a purity of ≥99.5%.
Preferably, the Crystalline form C is a methanol solvent compound.

The invention further provides another crystalline form of the compound of Formula I, hydrates and/or solvates thereof and its X-ray powder diffraction pattern has characteristic peaks at diffraction angles 2θ of 9.2±0.2°, 18.0±0.2° and 18.5±0.2°. To be convenient, the invention is regarded as Crystalline form D.

Secondly, the present invention further provides preferred embodiments of the above Crystalline form D:

Preferably, the X-ray powder diffraction pattern of the above Crystalline form D has the characteristic peaks at diffraction angles 2θ of 4.5±0.2°, 9.2±0.2°, 18.0±0.2°, 18.5±0.2°, 19.5±0.2° and 20.1±0.2°.

Preferably, the X-ray powder diffraction pattern of the above Crystalline form D has characteristic peaks at diffraction angles 2θ of 4.5±0.2°, 9.2±0.2°, 18.0±0.2°, 18.5±0.2°, 19.5±0.2°, 20.1±0.2°, 22.3±0.2° and 23.1±0.2°.

Preferably, the above Crystalline form D has an X-ray powder diffraction pattern approximately as shown in FIG. 4.

The present invention summarizes the X-ray powder diffraction pattern for Crystalline form D as shown in Table 4.

TABLE 4

| 2θ (°) | Intensity (I %) |
|---|---|
| 4.5 ± 0.2 | 21.9 |
| 9.2 ± 0.2 | 100 |
| 18.0 ± 0.2 | 54.5 |
| 18.5 ± 0.2 | 23.4 |
| 19.5 ± 0.2 | 13.2 |
| 20.1 ± 0.2 | 13.1 |
| 22.3 ± 0.2 | 11.8 |
| 23.1 ± 0.2 | 11.9 |

Preferably, the Crystalline form D has a purity of ≥85%.
Preferably, the Crystalline form D has a purity of ≥95%.
Preferably, the Crystalline form D has a purity of ≥99%.
Preferably, the Crystalline form D has a purity of ≥99.5%.
Preferably, the Crystalline form D is a dimethyl sulfoxide solvent compound.

The invention further provides another crystalline form of the compound of Formula I, hydrates and/or solvates thereof and its X-ray powder diffraction pattern has the characteristic peaks at diffraction angles 2θ of 4.8±0.2°, 9.6±0.2° and 25.8±0.2°. To be convenient, the invention is regarded as Crystalline form E.

Secondly, the present invention further provides preferred embodiments of the above Crystalline form E:

Preferably, the X-ray powder diffraction pattern of the above Crystalline form E has characteristic peaks at diffraction angles 2θ of 4.8±0.2°, 9.6±0.2°, 16.3±0.2°, 18.1±0.2°, 20.8±0.2° and 25.8±0.2°.

Preferably, the X-ray powder diffraction pattern of the above Crystalline form E has characteristic peaks at diffraction angles 2θ of 4.8±0.2°, 9.6±0.2°, 16.3±0.2°, 18.1±0.2°, 19.3±0.2°, 20.8±0.2°, 25.8±0.2° and 26.7±0.2°.

Preferably, the above Crystalline form E has an X-ray powder diffraction pattern approximately as shown in FIG. 5.

The present invention summarizes the X-ray powder diffraction pattern for Crystalline form E as shown in Table 5.

TABLE 5

| 2θ (°) | Intensity (I %) |
|---|---|
| 4.8 ± 0.2 | 47.1 |
| 9.6 ± 0.2 | 100 |
| 16.3 ± 0.2 | 34.1 |
| 18.1 ± 0.2 | 28.3 |
| 19.3 ± 0.2 | 24.9 |
| 20.8 ± 0.2 | 26.8 |
| 25.8 ± 0.2 | 41.6 |
| 26.7 ± 0.2 | 20.9 |

Preferably, the Crystalline form E has a purity of ≥85%.
Preferably, the Crystalline form E has a purity of ≥95%.
Preferably, the Crystalline form E has a purity of ≥99%.
Preferably, the Crystalline form E has a purity of ≥99.5%.
Preferably, the Crystalline form E is a dihydrate.

The present invention further provides amorphous forms of the compounds of Formula I, hydrates and/or solvates thereof, with an X-ray powder diffraction pattern approximately as shown in FIG. 6.

The invention further provides a pharmaceutical composition comprising a therapeutically effective amount of the above Crystalline form A and/or Crystalline form B.

The present invention also provides a preferred embodiment of the above pharmaceutical compositions:

Preferably, the pharmaceutical composition comprises a therapeutically effective amount of Crystalline form A or Crystalline form B provided herein, and a pharmaceutically acceptable excipient, adjuvant or carrier.

Preferably, the pharmaceutical composition comprises a therapeutically effective amount of Crystalline form A and Crystalline form B provided herein, and a pharmaceutically acceptable excipient, adjuvant or carrier.

Preferably, the pharmaceutical composition comprises a therapeutically effective amount of Crystalline form A or Crystalline form B of the invention in combination with at least one other effective component.

Preferably, the pharmaceutical composition comprises a therapeutically effective amount of Crystalline form A and Crystalline form B of the invention in combination with at least one other effective component.

Preferably, the pharmaceutical composition is in a form of an oral preparation.

Preferably, the pharmaceutical composition is in a form of a tablet or capsule.

Preferably, the pharmaceutical composition comprises 20 mg to 150 mg of Crystalline form A and/or Crystalline form B and is formulated in a total amount of about 50 mg to 500 mg with at least one excipient, adjuvant and/or carrier.

Preferably, the excipient, adjuvant and/or carrier in the pharmaceutical composition are microcrystalline cellulose, mannitol, crospovidone, croscarmellose sodium, sodium carboxymethyl starch, Povidone, hydroxypropyl cellulose and/or stearic acid.

Preferably, the pharmaceutical composition comprises 0.01 wt % to 99 wt % of Crystalline form A or Crystalline form B.

Preferably, the pharmaceutical composition comprises 0.01 wt % to 99 wt % of Crystalline form A and Crystalline form B.

Preferably, the pharmaceutical composition comprises 0.1 wt % to 70 wt % of Crystalline form A or Crystalline form B.

Preferably, the pharmaceutical composition comprises 0.1 wt % to 70 wt % of Crystalline form A and Crystalline form B.

Preferably, the pharmaceutical composition comprises 1 wt % to 70 wt % of Crystalline form A or Crystalline form B.

Preferably, the pharmaceutical composition comprises 1 wt % to 70 wt % of Crystalline form A and Crystalline form B.

Preferably, the pharmaceutical composition comprises 1 wt % to 50 wt % of Crystalline form A or Crystalline form B.

Preferably, the pharmaceutical composition comprises 1 wt % to 50 wt % of Crystalline form A and Crystalline form B.

Preferably, the pharmaceutical composition comprises 1 wt % to 30 wt % of Crystalline form A or Crystalline form B.

Preferably, the pharmaceutical composition comprises 1 wt % to 30 wt % of Crystalline form A and Crystalline form B.

Preferably, the pharmaceutical composition comprises 10 wt % to 30 wt % of Crystalline form A or Crystalline form B.

Preferably, the pharmaceutical composition comprises 10 wt % to 30 wt % of Crystalline form A and Crystalline form B.

The present invention also provides the use of Crystalline form A and/or Crystalline form B in preparation of a medicament for treating disease, disorder or condition in a patient, wherein the disease, disorder or condition is mediated by c-Met, RON, Axl, CSF1R, EphA2, ROS1 or ROS1 fusion protein, TRKA or TRKA fusion protein, TRKB, TRKC, ALK, ALK$^{ATI}$ or ALK fusion protein.

The invention also provides a preferred embodiment of the above use of Crystalline form A and/or Crystalline form B:

Preferably, ALK fusion protein is EML4-ALK or NPM-ALK kinase.

Preferably, the disease, disorder or condition is cancer and/or proliferative disease.

Preferably, the disease, disorder or condition is lung cancer, melanoma, colon cancer, breast cancer, liver cancer, pancreatic cancer, brain cancer, kidney cancer, ovarian cancer, gastric cancer, skin cancer, bone cancer, glioma, lymphoma, neuroblastoma, hepatocellular carcinoma, papillary renal cell carcinoma and/or head and neck squamous cell carcinoma.

Preferably, the disease, disorder or condition is non-small cell lung cancer (NSCLC) resistant to crizotinib therapy.

Preferably, the disease, disorder or condition is melanoma.

Preferably, the disease, disorder or condition is neurological disease, psychiatric disease, obesity, diabetes and/or cardiovascular disease.

Preferably, the psychiatric disease is schizophrenia, depression and/or substance addiction or abuse of substance.

Preferably, the addiction or abuse of substance is addiction or abuse of cocaine, tobacco or alcohol.

The present invention also provides a method for treating a disease, disorder or condition by administering Crystalline form A and/or Crystalline form B provided herein to the patient.

The present invention further provides preferred embodiments of the above-described method of treating a disease, disorder or condition of a patient utilizing Crystalline form A and/or Crystalline form B:

Preferably, the disease, disorder or condition is mediated by c-Met, RON, Axl, CSF1R, EphA2, ROS1 or ROS1 fusion protein, TRKA or TRKA fusion protein, TRKB, TRKC, ALK, ALK$^{ATI}$ or ALK fusion protein.

Preferably, ALK fusion protein is EML4-ALK or NPM-ALK kinase.

Preferably, the disease, disorder or condition is cancer and/or proliferative disease.

Preferably, the disease, disorder or condition is lung cancer, melanoma, colon cancer, breast cancer, liver cancer, pancreatic cancer, brain cancer, kidney cancer, ovarian cancer, gastric cancer, skin cancer, bone cancer, glioma, lymphoma, neuroblastoma, hepatocellular carcinoma, papillary renal cell carcinoma and/or head and neck squamous cell carcinoma.

Preferably, the disease, disorder or condition is non-small cell lung cancer (NSCLC) resistant to crizotinib therapy.

Preferably, the disease, disorder or condition is melanoma.

Preferably, the disease, disorder or condition is neurological disease, psychiatric disease, obesity, diabetes and/or cardiovascular disease.

Preferably, the psychiatric disease is schizophrenia, depression and/or addiction or abuse of substance.

Preferably, the addiction or abuse of the substance is the addiction or abuse of cocaine, tobacco or alcohol.

The present invention further provides preparation methods of the compound of formula I, as follows:

Method 1:

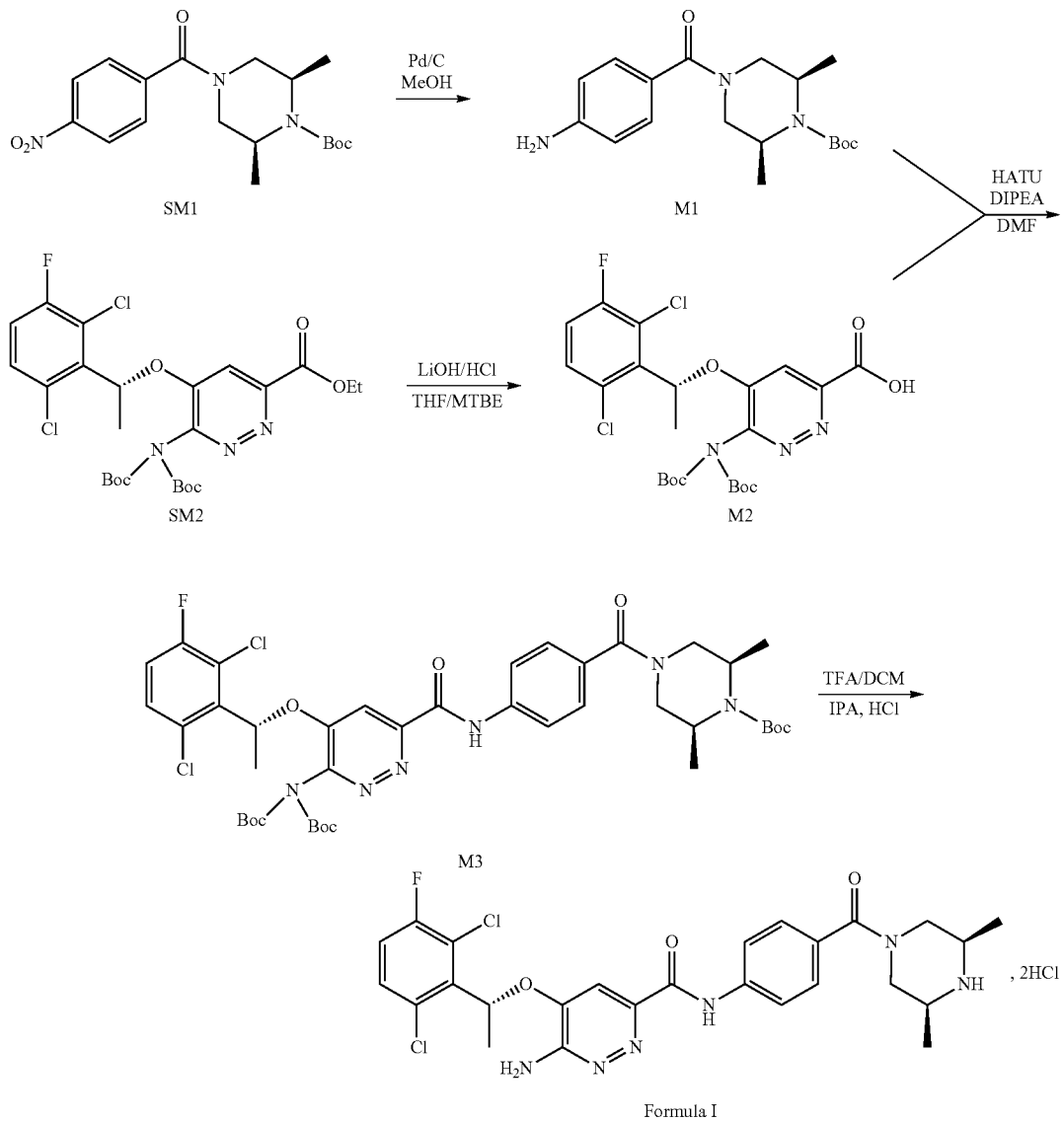

Method 2:
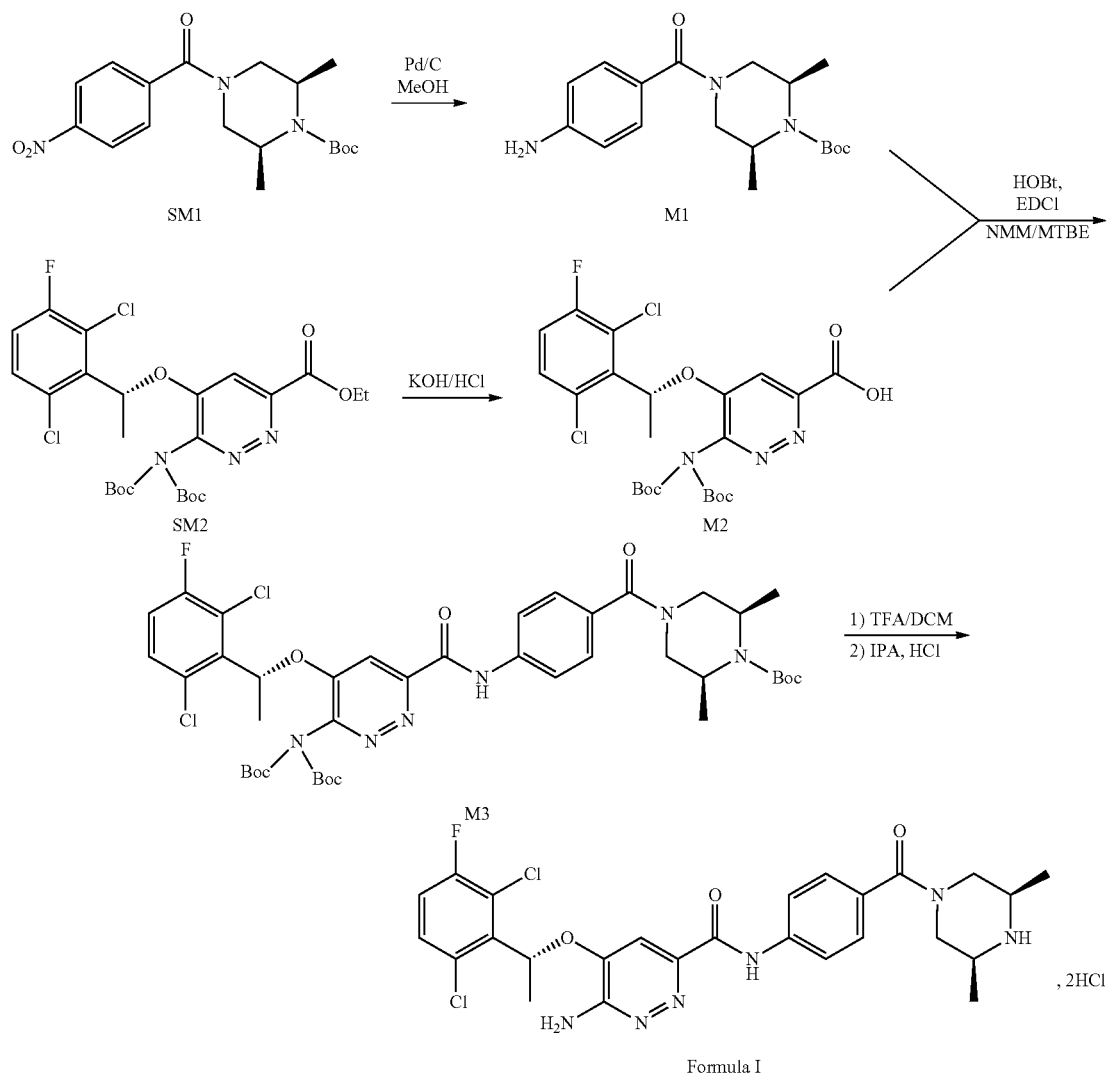
Method 3:
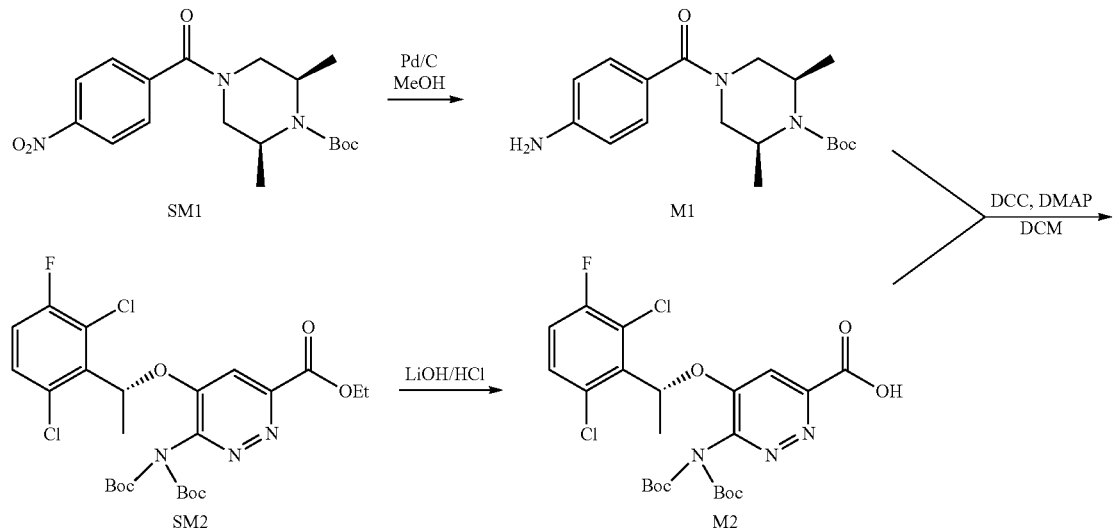

-continued

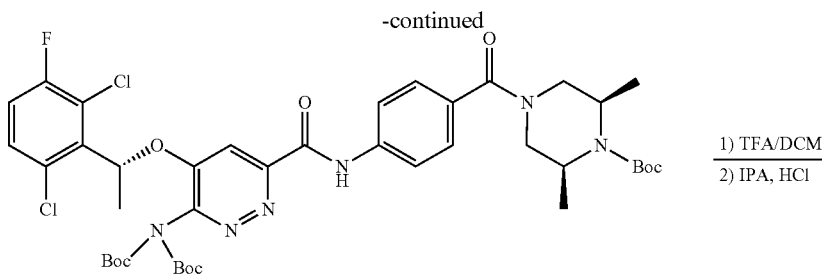

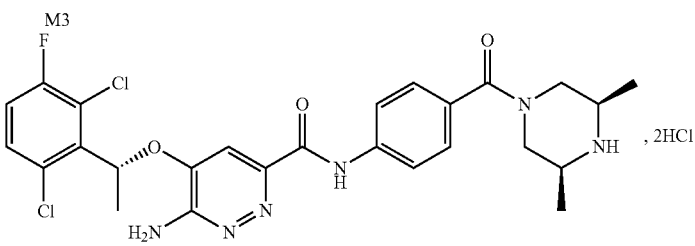

Formula I

The invention further provides intermediates in the preparation of the compound of formula I, as follows:

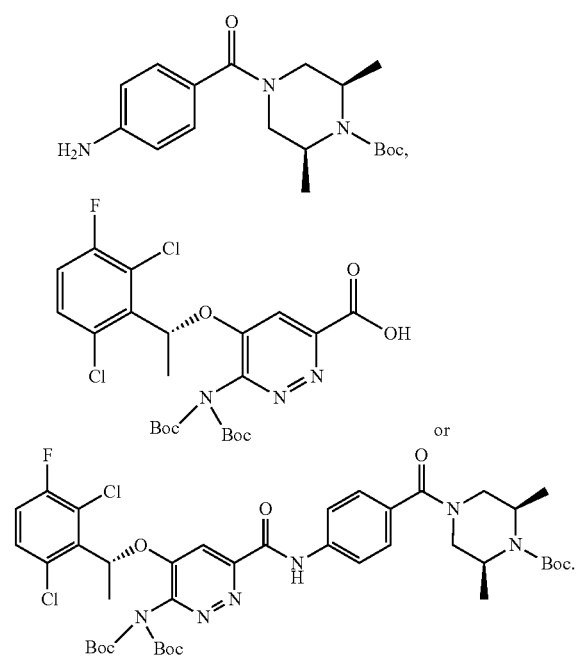

The invention further provides methods of preparing Crystalline form A and Crystalline form B of compounds of Formula I, hydrates and/or solvates thereof.

Wherein, Crystalline form A is prepared as follows:

an amorphous sample of the compound of formula I was placed in centrifuge tubes, and stored in an airtight ethanol or acetonitrile atmosphere for 6-10 days at room temperature to obtain the Crystalline form A; or, an amorphous sample of the compound of formula I was added into ethanol, stirred at 4° C. to 25° C., and filtrated to give the Crystalline form A; or, an amorphous sample of the compound of formula I was added into ethanol at 4° C. to 25° C., and dissolved to get a clear solution, the solution was filtered to give filtrate; then the filtrate was added with n-heptane under stirring until a large amount of crystal being observed, then filtered to obtain the Crystalline form A; or, an amorphous sample of the compound of formula I was added into methyl tert-butyl ether/ethanol or n-heptane/ethanol at 55° C. to 70° C., and dissolved to get a clear solution; and the solution was filtered to give filtrate; then the filtrate was stirred at −20° C. until solid being observed, and filtrated to obtain the Crystalline form A; or an amorphous sample of the compound of formula I was added into sec butyl alcohol, and dissolving to get a clear solution, filtrated, then exposed to 35° C. to 50° C. to evaporate solvent, giving the Crystalline form A; or, an amorphous sample of the compound of formula I was added into methanol, and dissolved to get a clear solution, the solution was filtered to give filtrate, then the filtrate was added with carboxymethyl cellulose, and exposed to room temperature to evaporate solvent, obtaining the Crystalline form A.

Wherein the method of preparing Crystalline form B is as follows:

the Crystalline form A was added into methanol, ethanol or water, dissolved to get a clear solution, filtered, then exposed to room temperature (20° C.) to 40° C. to evaporate solvent, obtaining the Crystalline form B; or, the Crystalline form A was added into methanol/water, methanol/acetone, methanol/ethyl acetate, methanol/methyl tert-butyl ether, methanol/tetrahydrofuran, methanol/dichloromethane, ethanol/water, ethanol/butanone, ethanol/isopropyl acetate, ethanol/n-heptane, trifluoroethanol/water, trifluoroethanol/ethyl acetate, trifluoroethanol/tetrahydrofuran, water/methanol, water/ethanol, water/trifluoroethanol, water/isopropanol, water/acetone, water/tetrahydrofuran or water/acetonitrile, dissolved to get a clear solution, then the solution was filtrated and exposed to room temperature (20° C.) to 40° C. to evaporate solvent, obtaining the Crystalline form B; or, the Crystalline form A was added into a lower alcohol, water, nitromethane, butanone, ethyl ether, ethyl acetate, tetrahydrofuran, toluene or n-heptane to form a suspension; then the suspension was stirred for 4 to 5 days at room temperature to 40° C., and centrifuged to obtain the Crystalline form B; or, the Crystalline form A was added into water-saturated ethyl acetate layer, a saturated aqueous layer of ethyl acetate, ethanol/diethyl ether, toluene/acetonitrile, butanone/ethanol or toluene/isopropyl ether to form suspension; then the suspension was stirred at 4° C. to 40° C. for 4-5 days and centrifuged to obtain the Crystalline form B; or, the Crystalline form A was added into methanol, acetone/water (3:1 v/v) or acetonitrile/water (3:2 v/v) at room temperature, and dissolved to get a clear solution; then the solution were added with hydroxypropylcellulose, ethylcellulose, povidone K30, polyallylamine hydrochloride, carboxymethylcellulose or polyvinyl alcohol, exposed to room temperature to evaporate solvent, obtaining the Crystalline form B; or, the Crystalline form A was added into a lower alcohol or water at 60° C.-70° C., dissolved to get a clear solution, and stirred at 4° C. until crystal being observed, obtaining the Crystalline form B; or, the Crystalline form A was added into acetone/trifluoroethanol, acetone/water, dioxane/water, acetonitrile/water or methyl t-butyl ether/n-propanol at 55° C. to 70° C., dissolved to get a clear solution; and the solution was filtrated to give filtrate, then the filtrate was stirred at −20° C. until crystal being observed, then filtered to give the Crystalline form B; or, the Crystalline form A was added into nitromethane/methanol, acetonitrile/methanol, butanone/ethanol, ethyl acetate/ethanol, 1,4-dioxane/ethanol or tetrahydrofuran/water at 60° C. to 70° C., and dissolved to get a clear solution, filtered and exposed to room temperature to evaporate solvent, obtaining the Crystalline form B; or, the Crystalline form A was added into methanol, ethanol, water, trifluoroethanol, n-propanol or dimethyl sulfoxide at room temperature, and dissolved to get a clear solution; the solution was filtrate, and the filtrate was added dropwise with acetone, ethyl acetate, methyl t-butyl ether, isopropyl ether, isopropyl acetate, tetrahydrofuran, 1,4-dioxane, acetonitrile, n-heptane, dichloromethane or chloroform until a large amount of crystal being observed, obtaining the Crystalline form B; or, the Crystalline form A was added into methanol or ethanol at room temperature, and dissolved to get a clear solution; and the solution was then filtrated to give filtrate; then the filtrate was added with dichloromethane or tetrahydrofuran under stirring, and exposed to room temperature to evaporate solvent, obtaining the Crystalline form B; or, an amorphous sample of the compound of formula I was placed in centrifuge tubes, and then the centrifuge tubes were placed in the atmosphere of n-butanol, water, nitromethane, ethyl acetate, methyl tert-butyl ether, tetrahydrofuran, methylene chloride, chloroform or toluene to diffuse, to give the Crystalline form B; or, an amorphous sample of the compound of formula I was added to n-propanol, water, butanone, ethyl acetate, tetrahydrofuran, dichloromethane, ethanol, isopropanol, n-butanol, acetone, ethyl ether, isopropyl acetate, 1,4-dioxane, acetonitrile, chloroform, sec-butanol, nitromethane or toluene, stirred at 4° C. to 40° C. for 30 minutes, then filtered to give the Crystalline form B; or, an amorphous sample of the compound of formula I was added into isopropyl ether/methanol, ethyl acetate/methanol, 1,4-dioxane/methanol, butanone/ethanol, acetonitrile/ethanol, n-heptane/ethanol, nitromethane/trifluoroethanol, ether/trifluoroethanol, tetrahydrofuran/trifluoroethanol, acetone/water, tetrahydrofuran/water, acetonitrile/water, methyl tert-butyl ether/isopropanol, isopropyl acetate/n-propanol, methylcyclohexane/n-butanol, acetone/dimethyl sulfoxide, ethyl acetate/dimethyl sulfoxide, acetonitrile/dimethyl sulfoxide, methyl tert-butyl ether/chloroform or toluene/ethyl acetate to form a suspension, stirred at 4° C. to 40° C., then filtered to give the Crystalline form B; or, an amorphous sample of the compound of formula I was placed at room temperature at a humidity of 85% RH for 10 days to obtain the Crystalline form B; or, the Crystalline form A was added into water or methanol, and dissolved to get a clear solution; the solution was filtrated to give filtrate; then the filtrate was rotary evaporated to dry at 40° C.-60° C., obtaining the Crystalline B.

The Crystalline forms of the present invention is approximately pure.

The term "approximately pure" as herein used refers to at least 85 wt %, preferably at least 95 wt %, more preferably at least 99 wt %, most preferably at least 99.5 wt % of the compound as shown in formula I exists in the Crystalline form of the present invention. Particularly in the Crystalline form A and/or Crystalline form B.

The above crystalline forms only summarize the major peaks. The main peaks are reproducible and are within the error limits (±0.2).

In the present invention, "the X-ray powder diffraction pattern being shown as in FIG. 1" or "the X-ray powder diffraction pattern being shown as in FIG. 2", refers to the X-ray powder diffraction pattern that shows major peaks as in FIG. 1 or FIG. 2, wherein major peaks refer to those with the relative intensity greater than 10%, preferably greater than 30%, relative to the highest peak (with its relative intensity designated to be 100%) in FIG. 1 or FIG. 2.

In the present invention, "added into methanol/acetone" which is involved in the method of preparing Crystalline form A or Crystalline form B means that in the method methanol was added first, and then acetone was added. Similarly, "ethanol/water" means that ethanol was added first, and then water was added; and "trifluoroethanol/ethyl acetate" means trifluoroethanol was added first and then ethyl acetate was added. In a similar way, for example, "solvent 1/solvent 2" means that solvent 1 was added first and then solvent 2 was added; and "solvent 2/solvent 1" means that solvent 2 was added first and then solvent 1 was added.

In the present invention, The term "therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

All formulations of the pharmaceutical composition of the present invention can be produced by the conventional methods in the pharmaceutical field. For example, the active ingredient can be mixed with one or more excipients, then to make the desired formulation.

The "pharmaceutically acceptable carriers" refers to conventional pharmaceutical carriers suitable for the desired pharmaceutical formulation, for example: a diluent, excipient such as water, various organic solvents, etc.; a filler such as starch, sucrose, etc.; a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye. Preferably, the excipient is suitable for desired formulation and administration type.

The term "disease" or "disorder" or "condition" refers to any disease, discomfort, illness, symptoms or indications.

Table 6 summarizes the detection equipment and methods of the X-ray powder diffraction pattern shown in FIGS. 1-6.

Figure 7:
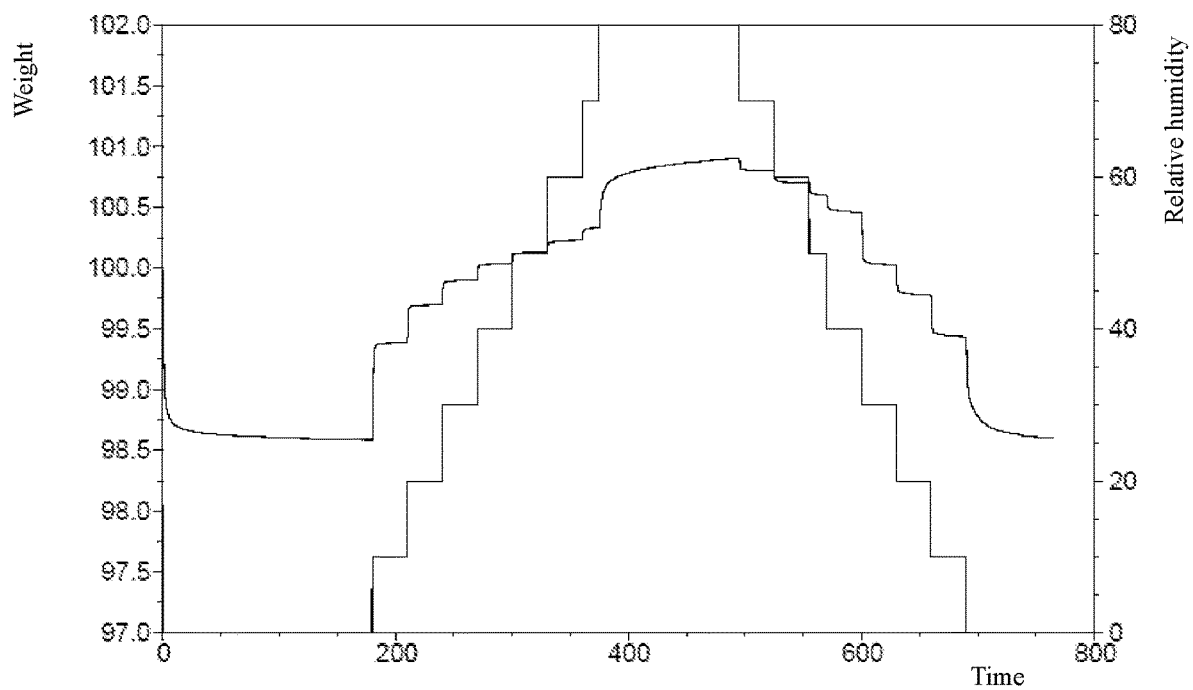
FIG. 7: Dynamic water adsorption pattern of Crystalline form A of the compound as shown in formula I.
Figure 8:
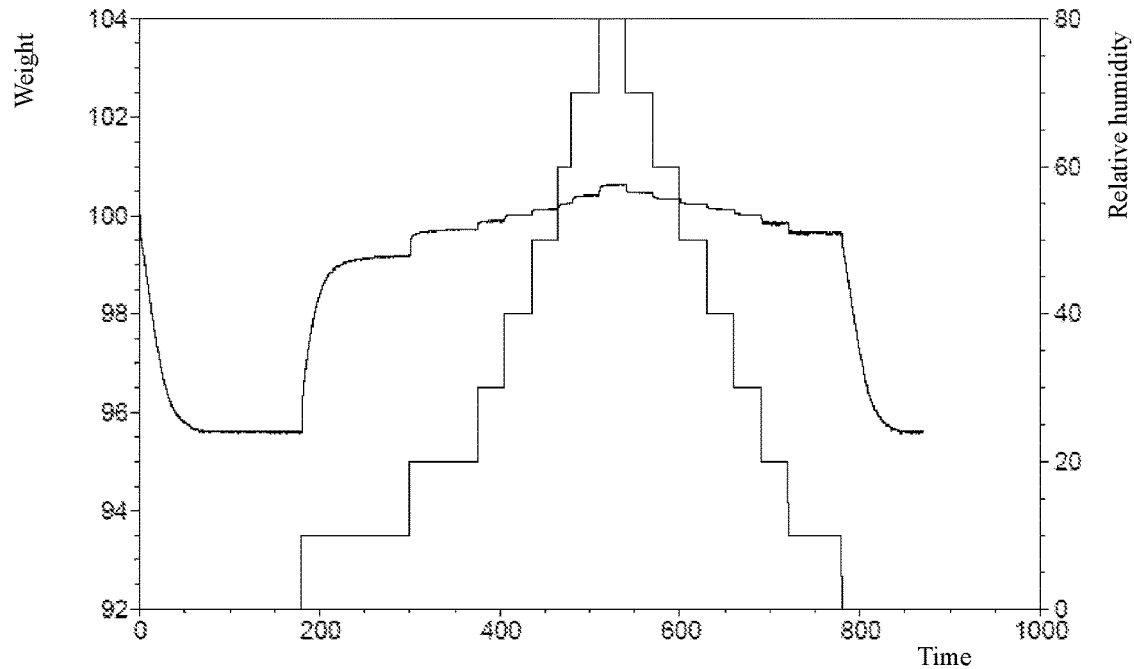
FIG. 8: Dynamic water adsorption pattern of Crystalline form B of the compound as shown in formula I.
Figure 9:
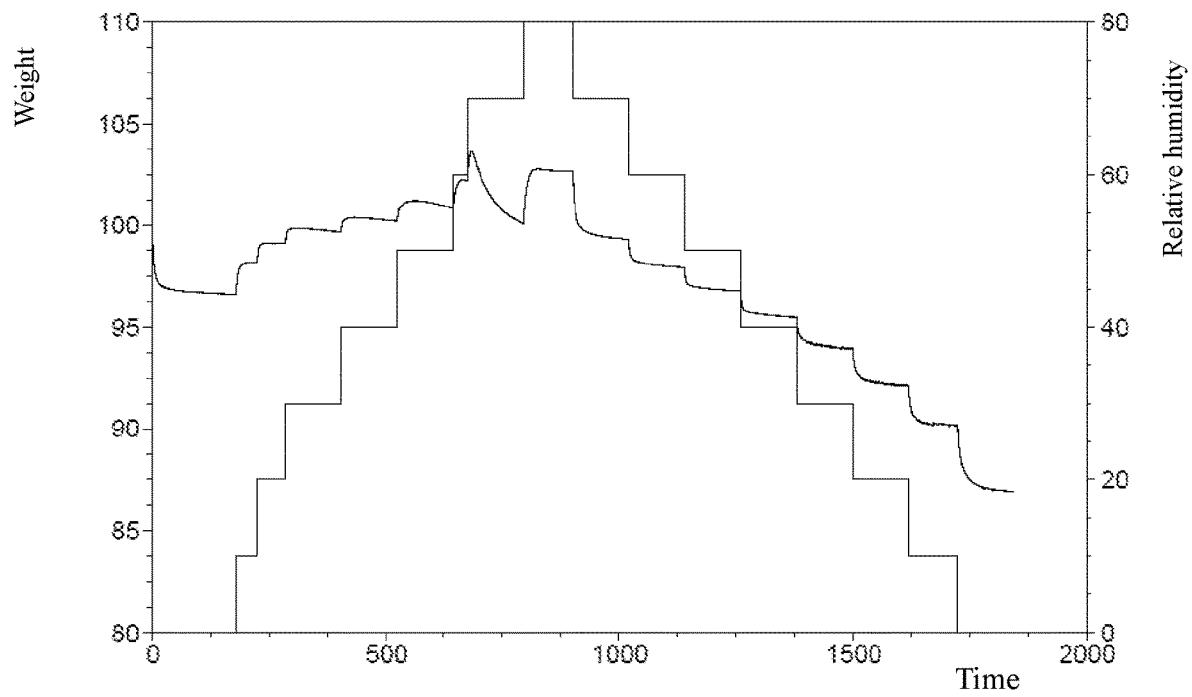
FIG. 9: Dynamic water adsorption pattern of amorphous sample of the compound as shown in formula I.

Table 7 summarizes the detection equipment and methods of the dynamic water adsorption pattern shown in FIGS. 7-9.

Figure 10:
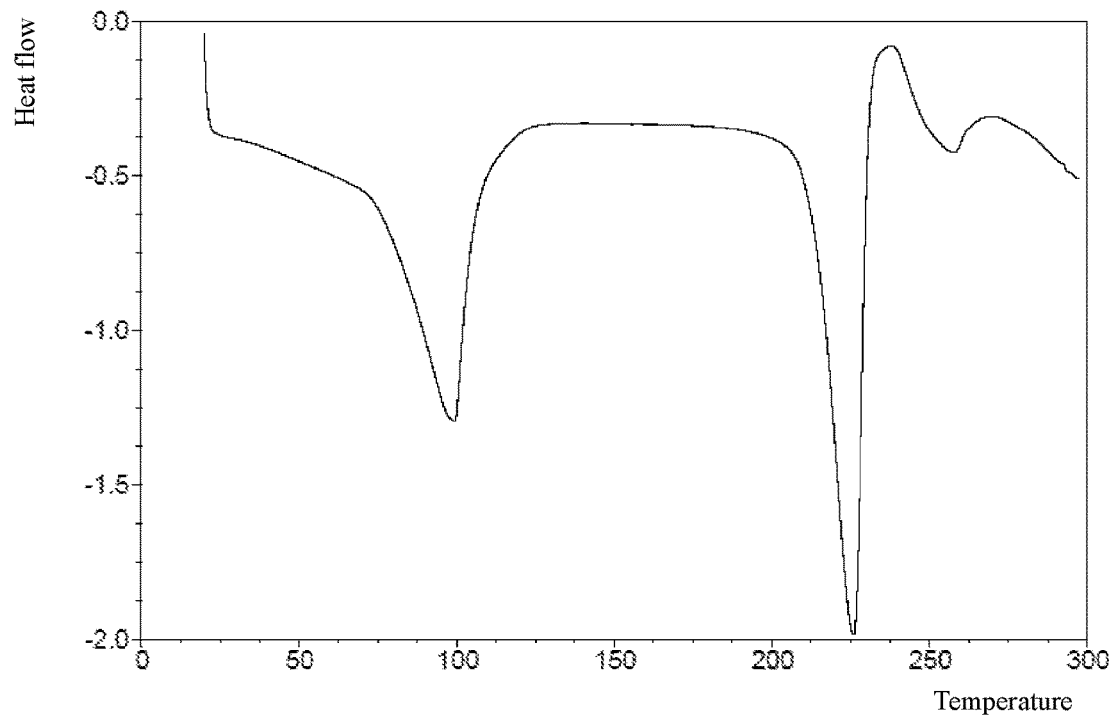
FIG. 10: The differential thermal analysis of Crystalline form A of the compound as shown in formula I.
Figure 11:
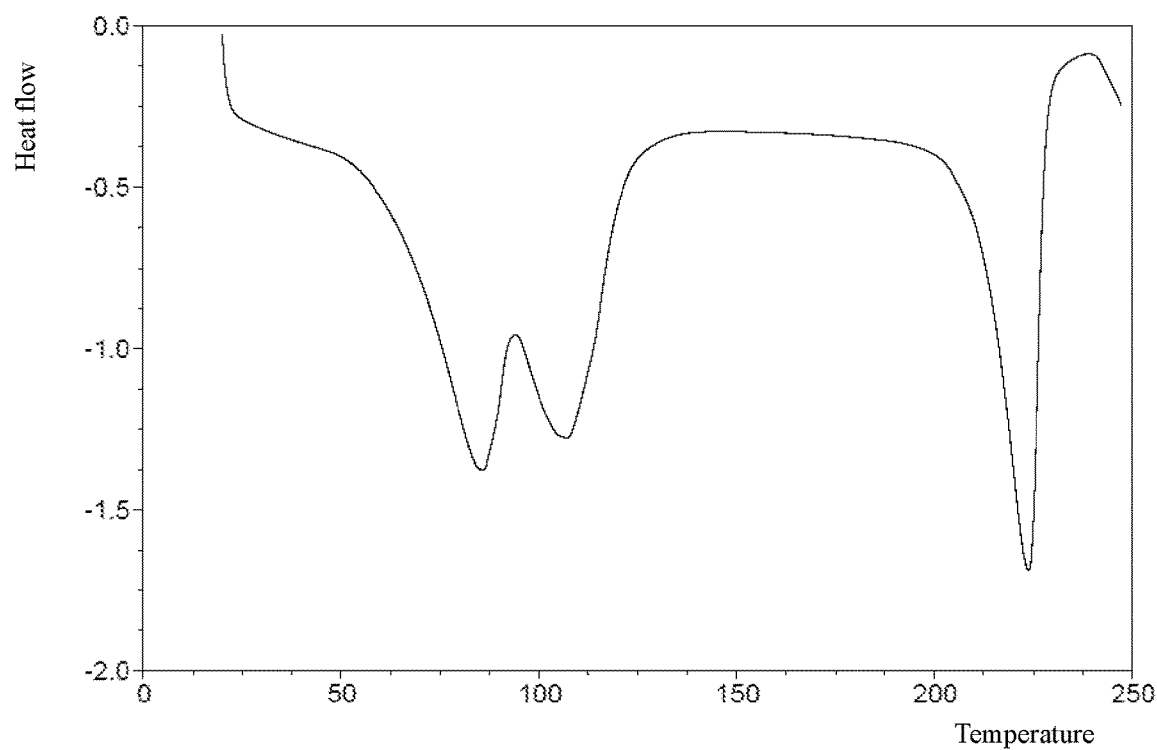
FIG. 11: The differential thermal analysis of Crystalline form B of the compound as shown in formula I.
Figure 12:
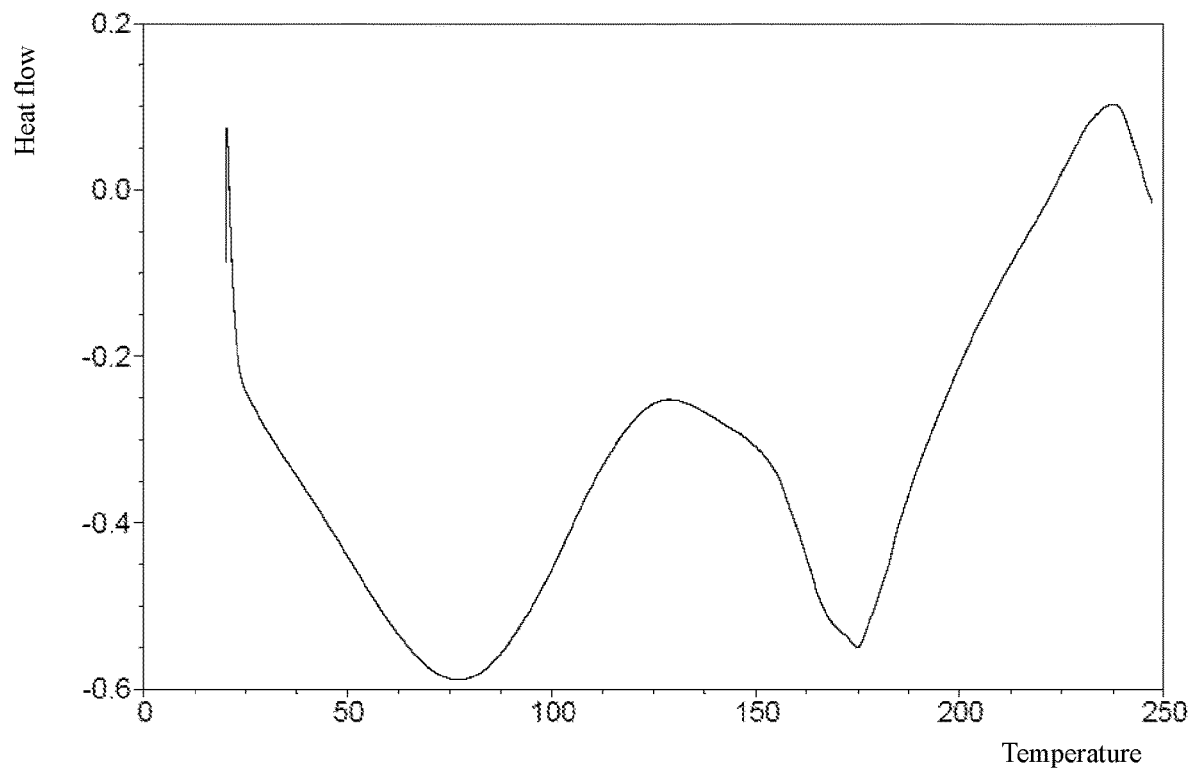
FIG. 12: The differential thermal analysis of amorphous sample of the compound as shown in formula I.

Table 8 summarizes the detection equipment and methods of the differential thermal analysis of scanning pattern shown in FIGS. 10-12.

TABLE 6

| Device name | X-ray powder diffractometer (XRD) & Hot stage XRD | |
|---|---|---|
| Equipment | Bruker D8 Advance diffractometer | |
| Technical Specifications | Kα radiation (40 Kv, 40 Ma) copper target wavelength: 1.54 nm, θ-2θ goniometer, Mo monochromator, Lynxeye detector | |
| Calibrated substance | $Al_2O_3$ | |
| Acquisition software | Diffrac Plus XRD Commander | |
| Analysis software | MDI Jade 6 | |
| Method parameters | Non reflective sample plate specification | 24.6 mm diameter × 1.0 mm Thickness |
| | Variable temperature hot stage sample plate | Copper plate |
| | Detection angle | 3-40°2θ/3-30°2θ (Hot stageXRD) |

TABLE 6-continued

| Step length | 0.02°2θ |
|---|---|
| Speed | 0.2 s.step-1 |
| detected sample weight | >2 mg |

TABLE 7

| Device name | Dynamic Vapor Sorption (DVS) | |
|---|---|---|
| Instrument | TA Instruments Q5000TGA | |
| Control software | Thermal Advantage | |
| Analysis software | Universal Analysis | |
| Sample plate | Platinum crucible | |
| detected sample weight | 1-10 mg | |
| Protective gas | Nitrogen | |
| Gas flow rate | 10 mL/min | |
| Detection method | Equilibrate at 20° C.; Humidity 0% ; Isothermal for 180 min; Abort next iso if weight (%) < 0.0100 for 15.00 min; step humidity 10% every 120 min to 80.00%; Abort next iso if weight(%) <0.0100 for 15.00 min; step humidity 10% every 120 min to 0.00% | |
| Judgment standard | non-hygroscopic | Not more than 0.2% |
| | Mild hygroscopic | More than 0.2% , but not more than 2.0% |
| | Hygroscopic | More than 2% , but not more than 15% |
| | Extremely hygroscopic | More than 15% |

TABLE 8

| Device name | Differential thermal analysis scanner (DSC) |
|---|---|
| Instrument | TA Instruments Q200 DSC |
| Control software | Thermal Advantage |
| Analysis software | Universal Analysis |
| Sample plate | Aluminum crucible (sealed and punched) |
| detected sample weight | 0.5-5 mg |
| Protective gas | Nitrogen |
| Gas flow rate | 40 mL/min |
| Common detection methods | Equilibrate at 20° C.; Ramp 10° C./min to 250/300° C. |

EXAMPLES

The present invention is further exemplified, but not limited, by the following examples that illustrate the invention. In the examples of the present invention, the techniques or methods, unless expressly stated otherwise, are conventional techniques or methods in the art.

Abbreviations

Boc: Butoxycarbonyl;
DCC: Dicyclohexylcarbodiimide;
DCM: Dichloromethane;
DIPEA: Diisopropylethylamine;
DMAP: 4-diMethylaMinopyridine;
DMF: N,N-Dimethylformamide;
EDCI: 1-ethyl-(3-dimethylaminopropyl) carbodiimide hydrochloride;
HATU: 2-(7-Azabenzotriazol-1-yl)-N,N,N',N'-tetramethyluronium hexafluorophosphate;
HOBT: 1-Hydroxybenzotriazole;
IPA: Isopropyl alcohol;
MeOH: Methanol;
MTBE: Methyl tert-butyl ether;

NMM: N-methylmorpholine;
N: mol/L;
TFA: Trifluoroacetate;
THF: Tetrahydrofuran.

Example 1: Synthesis of the Compounds of Formula I

Synthesis of Compound M1:

8.57 g (0.024 mol, 1.00 eq) of Compound SM1 was dissolved in 85.7 mL of anhydrous methanol and 5% palladium on carbon (0.86 g) was added under nitrogen. The mixture was replaced with hydrogen three times and reacted in the atmosphere of hydrogen for 3 hours. When the reaction of the raw materials was complete, the filtrate was collected by filtration, then concentrated to solid and dried under vacuum to give the white solid, that is compound M1 with a yield of 100% and a purity of 97.32%.

LC-MS[M+H$^+$]: 334.

Synthesis of Compound M2:

The 9.60 g (0.017 mol, 1.00 eq) of compound SM2 was dissolved in 53 mL of THF, the reaction mixture was cooled to −5 to 5° C. 1N KOH aqueous solution (1.40 g KOH and 25 mL water) was added dropwise and the mixture was incubated at 1 to 10° C. and stirred for 4 hours. 1N dilute hydrochloric acid was added to adjust pH value to about 5. The mixture was extracted with ethyl acetate (50 mL×2) twice. The organic layers were combined and washed with saturated salt water solution, dried over anhydrous sodium sulfate for 1 hour, followed by filtered, and concentrated under vacuum to obtain viscous oil, 23 mL of dichloromethane was add to dissolve the above viscous oil, and then concentrated under vacuum to get a thick oil again. 69 mL of dichloromethane was add to dissolve the thick oil again and concentrated under vacuum to obtain 9.10 g of intermediate M2 as a yellow solid with a yield of 99.7%.

LC-MS[M+H$^+$]: 546.

Synthesis of Compound M2:

9.60 g (0.017 mol, 1.00 eq) of compound SM2 was dissolved in 53 mL of THF and the reaction mixture was cooled to 0-10° C. 1N of LiOH aqueous solution (1.05 g LiOH+25 mL water) was added dropwise. After 30 minutes of addition, the temperature gradually increased to room temperature, and reaction mixture were stirred overnight. The reaction was completed and concentrated under vacuum. The resulting residue was dissolved in 100 mL of water, and 50 mL of methyl tert-butyl ether was added, stirred and separated. 1N of dilute hydrochloric acid was added dropwise to the water phase for adjusting pH value to about 5. The mixture was extracted with ethyl acetate (50 mL×2) twice. The organic layers were combined and washed with saturated salt water solution and dried over anhydrous sodium sulfate for 1 hour. The mixture was filtered and evaporated under vacuum to obtain 8.58 g of intermediate M2 as a yellow solid. The yield was 94%.

LC-MS[M+H$^+$]: 546.

Synthesis of Compound M3:

8.23 g (0.015 mol, 1.15 eq) of compound M2 was dissolved in 66 mL of dichloromethane and cooled to 10 to 20° C. 4.30 g (0.013 mol, 1.00 eq) of compound M1, 3.00 g (0.022 mol, 1.69 eq) of Hydroxybenzotriazole (HOBT), 4.58 g (0.024 mol, 1.85 eq) of 1-ethyl-(3-dimethylaminopropyl) carbodiimide hydrochloride (EDCI) and 6.90 g (0.068 mol, 5.23 eq) of N-methylmorpholine (NMM) was added in turn. The mixture was incubated and stirred at 20 to 30° C. for 16 hours, 16 mL of water was added to the reaction mixture, stirred for 10-15 minutes, liquid was separation when still, 16 mL of 1N diluted hydrochloric acid was added to the organic layer, stirred for 5 minutes, liquid was separation when still; the organic layer was washed by 16 mL of 1N dilute hydrochloric acid, 5 mL of 1N KOH water solution and 30 mL of saturated salt water respectively, and the static liquid was separated. The organic phase was dried by anhydrous sodium sulfate, followed by filtered and concentrated in vacuum. The resulting residue was washed with methyl tert-butyl ether (20 mL+20 mL+6 mL) for three times, and filtration was to collected solid, the solid was dried to give 7.95 g of yellow-like solid as the compound M3 with a yield of 71.6%.

LC-MS[M+H$^+$]: 861.

Synthesis of Compound M3:

7.96 g (0.015 mol, 1.15 eq) of compound M2 was dissolved in 40 mL of DMF, to which was added 5.23 g (0.014 mol, 1.08 eq) of HATU, 4.17 g (0.013 mol, 1.00 eq) of compound M1 and 2.17 mL of diisopropylethyl amine. The reaction mixture was stirred overnight at room temperature. 50 mL of saturated sodium carbonate aqueous solution was added to the reaction system, followed by stirred and filtered. The resulting solid is beaten with 60 mL of water and then filtered. The solid was dissolved in 30 mL of dichloromethane, washed twice with water, and the organic phase was dried, filtered, concentrated in vacuum and dried to obtain 10.03 g of compound M3 as brown solid with a yield of 93.2%.

LC-MS[M+H$^+$]: 861.

Synthesis of Compound M3:

The 9.77 g of (0.018 mol, 1.20 eq) compound M2 was dissolved in 75 mL of dichloromethane, to which was added 6.21 g (0.030 mol, 2.00 eq) of dicyclohexylcarbodiimide, 0.96 g (0.0079 mol, 0.53 eq) of DMAP, and 5.00 g (0.015 mol, 1.00 eq) of compound M1. The reaction mixture was stirred overnight at room temperature. 20 mL of water was added to the reaction system, stirred and the liquid was separation when still; 20 mL of 1N dilute hydrochloric acid was added to the organic phase, stirred for 5 minutes, the liquid was separation when still. The organic layer was washed by 20 mL of dilute hydrochloric acid, 6 mL of 1N KOH water solution and 35 mL of saturated salt water respectively, and the static liquid was separated. The organic phase was dried by anhydrous sodium sulfate, filtered, and concentrated in vacuum. The resulting residue was washed for three times by adding methyl tert-butyl ether (25 mL+25 mL+8 mL). Filtration was to collect solid, and the solid was dried to obtain 10.62 g of brown solid as the compound M3 with a yield of 82.3%.

LC-MS[M+H$^+$]: 861.

Synthesis of the Compound of Formula I:

The 7.95 g (0.092 mol) of compound M3 was dissolved in 30 mL of dichloromethane, the reaction solution was cooled to −5° C. to 5° C., to which was dropped 15 mL of trifluoroacetate with stirring at room temperature for 2 hours. After the mixture was cooled to 10 to 20° C., to which the reaction mixture was slowly added 60 mL of saturated potassium carbonate aqueous solution, followed by stirred and static stratification. The organic layer was washed with saturated salt water, and dried over by anhydrous sodium sulfate, followed by filtered and concentrated. The resulting residue was dissolved in 41.2 g of isopropanol, after the mixture was cooled to 10 to 20° C., to which the reaction mixture was added 5 mL of concentrated hydrochloric acid with stirring at room temperature. Filtration was to collect solid, and the solid was washed by isopropanol, dried in vacuum to obtain 5.75 g of compound of formula I.

LC-MS[M+H$^+$]: 561.

1H-NMR (300 MHz, CDCl$_3$): δ=1.25-1.43 (m, 6H), 1.91 (d, 3H), 3.15-3.48 (m, 4H), 3.66-3.89 (m, 0.5H), 4.55-4.78 (m, 0.5H), 5.49 (s, 2H), 6.26 (q, 1H), 7.10 (t, 1H), 7.33-7.44 (m, 4H), 7.78 (d, 2H), 9.93 (s, 1H).

Example 2: Preparation Method of Crystalline Form A

Preparation Method 1 of Crystalline Form A

About 5 to 10 mg of the amorphous compound of the Formula I was dissolved into sec-butanol to get a clear solution, followed by filtration, the solution was exposed to 40° C. to get the Crystalline Form A.

Preparation Method 2 of Crystalline Form A

About 10 mg of amorphous compound of the Formula I was dissolved into methanol to get a clear solution, followed by filtration, to which was added 1 mg of carboxymethyl cellulose. The mixture was exposed to room temperature to get the Crystalline Form A.

Preparation Method 3 and 4 of Crystalline Form A

At the corresponding temperature, about 10 mg of amorphous compound of the Formula I was added to Solvent 2, followed by added to Solvent 1 to get a clear solution and then filtered, stirred under −20° C. to precipitate solid, The precipitate was collected by filtration to obtain the Crystalline Form A.

| No. | Temperature (° C.) | Sample weight (mg) | Solvent 1 | Solvent 1 (volume, mL) | Solvent 2 | Solvent 2 (volume, mL) |
|---|---|---|---|---|---|---|
| preparation method 3 of the Crystalline Form A | 55 | 10 | Ethanol | 0.8 | Methyl tert-butyl ether | 1.0 |
| preparation method 4 of the Crystalline Form A | 70 | 10 | Ethanol | 0.8 | N-heptane | 0.8 |

Preparation Method 5 of Crystalline Form A

At room temperature, about 10 mg of amorphous compound of Formula I was dissolved into ethanol to get a clear solution, followed by filtration. n-heptane was dropped to the solution under stirring until a large amount of solid being observed, filtered and recovered the Crystalline Form A.

Preparation Method 6 and 7 of Crystalline Form A

Approximately 10 mg of the amorphous compound of Formula I was placed in 2.0 mL centrifuge tube and exposed at room temperature for 6 days in corresponding closed solvent atmosphere. The crystalline form A was obtained.

| No. | Sample weight (mg) | Solvent | Solvent (Volume, mL) |
|---|---|---|---|
| preparation method 6 of the Crystalline Form A | 10 | Ethanol | 4.0 |
| preparation method 7 of the Crystalline Form A 7 | 10 | Acetonitrile | 4.0 |

Preparation Method 8 of Crystalline Form A

Approximately 15 mg of the amorphous compound of Formula I was added to 0.2 mL of ethanol at 4° C., the mixture was stirred at the corresponding temperature for 30 minutes and filtered to obtain the Crystalline form A.

Example 3: Preparation Method of Crystalline For B

The First Experiment Method

About 5 to 10 mg of Crystalline form A was dissolved into the appropriate solvent to get a clear solution and then filtered. The mixture was exposed to the corresponding temperature for volatilization to get the Crystalline form B.

| No. | Temperature (° C.) | Crystalline Form A Weight (mg) | Solvent | Solvent (Volume, mL) |
|---|---|---|---|---|
| Preparation method 1 of Crystalline Form B | Room temperature | 5 | Methanol | 0.4 |
| Preparation method 2 of Crystalline Form B | Room temperature | 5 | Ethanol | 1.0 |
| Preparation method 3 of Crystalline Form B | Room temperature | 5 | Water | 0.1 |
| Preparation method 4 of Crystalline Form B | 40 | 10 | Ethanol | 1.5 |
| Preparation method 5 of Crystalline Form B | 40 | 10 | Water | 0.4 |

The Second Experiment Method

About 10 mg of Crystalline form A was added to solvent 1, followed by added to solvent 2 to get a clear solution and filtered, then exposed to the corresponding temperature for volatilization to obtain the Crystalline form B.

| No. | Temperature (° C.) | Crystalline Form A Weight (mg) | Solvent 1 | Solvent 1 (Volume, mL) | Solvent 2 | Solvent 2 (Volume, mL) |
|---|---|---|---|---|---|---|
| Preparation method 6 of Crystalline Form B | Room temperature | 10 | Methanol | 0.4 | Water | 0.1 |
| Preparation method 7 of Crystalline Form B | Room temperature | 10 | Methanol | 0.4 | Acetone | 0.4 |
| Preparation method 8 of Crystalline Form B | Room temperature | 10 | Methanol | 0.6 | Ethyl acetate | 0.4 |
| Preparation method 9 of Crystalline Form B | Room temperature | 10 | Methanol | 1.0 | Methyl tert-butyl ether | 0.4 |
| Preparation method 10 of Crystalline Form B | Room temperature | 10 | Methanol | 0.6 | Tetrahydrofuran | 0.6 |
| Preparation method 11 of Crystalline Form B | Room temperature | 10 | Methanol | 0.4 | Dichloromethane | 0.4 |
| Preparation method 12 of Crystalline Form B | Room temperature | 10 | Ethanol | 1.2 | Water | 0.2 |
| Preparation method 13 of Crystalline Form B | Room temperature | 10 | Ethanol | 1.2 | Butanone | 0.4 |
| Preparation method 14 of Crystalline Form B | Room temperature | 10 | Ethanol | 1.2 | Isopropyl acetate | 0.4 |
| Preparation method 15 of Crystalline Form B | Room temperature | 10 | Ethanol | 1.2 | n-Heptane | 0.4 |
| Preparation method 16 of Crystalline Form B | Room temperature | 10 | Trifluoro ethanol | 0.2 | Water | 0.2 |
| Preparation method 17 of Crystalline Form B | Room temperature | 10 | Trifluoro ethanol | 0.2 | Ethyl acetate | 0.2 |
| Preparation method 18 of Crystalline Form B | Room temperature | 10 | Trifluoro ethanol | 0.2 | Tetrahydrofuran | 0.4 |
| Preparation method 19 of Crystalline Form B | 40 | 10 | Water | 0.2 | Methanol | 0.6 |
| Preparation method 20 of Crystalline Form B | 40 | 10 | Water | 0.2 | Ethanol | 0.6 |
| Preparation method 21 of Crystalline Form B | 40 | 10 | Water | 0.2 | Trifluoroethanol | 0.4 |
| Preparation method 22 of Crystalline Form B | 40 | 10 | Water | 0.2 | Isopropanol | 0.4 |
| Preparation method 23 of Crystalline Form B | 40 | 10 | Water | 0.2 | Acetone | 1.0 |
| Preparation method 24 of Crystalline Form B | 40 | 10 | Water | 0.2 | Tetrahydrofuran | 0.6 |
| Preparation method 25 of Crystalline Form B | 40 | 10 | Water | 0.2 | Acetonitrile | 0.4 |

The Third Experiment Method

About 15 to 30 mg of Crystalline form A was added to the corresponding solvent to form suspension, stirred at room temperature for 5 days, filtered to obtain the Crystalline form B.

| No. | Temperature (° C.) | Crystalline form A weight (mg) | Solvent | Solvent (volume, mL) |
|---|---|---|---|---|
| Preparation method 26 of Crystalline Form B | Room temperature | 15 | Ethanol | 1.0 |
| Preparation method 27 of Crystalline Form B | Room temperature | 15 | Isopropanol | 2.0 |
| Preparation method 28 of Crystalline Form B | Room temperature | 15 | Propanol | 1.0 |
| Preparation method 29 of Crystalline Form B | Room temperature | 30 | Water | 0.4 |
| Preparation method 30 of Crystalline Form B | Room temperature | 15 | Nitromethane | 2.0 |
| Preparation method 31 of Crystalline Form B | Room temperature | 15 | Butanone | 2.0 |
| Preparation method 32 of Crystalline Form B | Room temperature | 15 | Ether | 2.0 |

The Fourth Experiment Method

About 15 to 20 mg of Crystalline form A was added to the corresponding solvent to form suspension, stirred for 5 days at 40° C., filtered to obtain the Crystalline form B.

| No. | Temperature (° C.) | Crystalline form A weight (mg) | Solvent | Solvent (Volume, mL) |
|---|---|---|---|---|
| Preparation method 33 of Crystalline Form B | 40 | 20 | Ethanol | 1.0 |
| Preparation method 34 of Crystalline Form B | 40 | 15 | Ethyl acetate | 2.0 |
| Preparation method 35 of Crystalline Form B | 40 | 15 | Tetrahydrofuran | 2.0 |
| Preparation method 36 of Crystalline Form B | 40 | 15 | Toluene | 2.0 |
| Preparation method 37 of Crystalline Form B | 40 | 15 | n-Heptane | 2.0 |

The Fifth Experiment Method

About 15 to 40 mg of Crystalline form A was added to Solvent 2 first, then added to Solvent 1 to form suspension, and stirred at the corresponding temperature for 4 days, filtered to obtain the Crystalline form B.

| No. | Temperature (° C.) | Crystalline form A weight (mg) | Solvent 1 | Solvent 1 (Volume, mL) | Solvent 2 | Solvent 2 (Volume, mL) |
|---|---|---|---|---|---|---|
| Preparation method 38 of Crystalline Form B | Room temperature | 20 | Water-saturated ethyl acetate layer | 2.0 | Non | Non |
| Preparation method 39 of Crystalline Form B | Room temperature | 40 | Ethyl acetate-saturated water layer | 0.5 | Non | Non |
| Preparation method 40 of Crystalline Form B | 4 | 15 | Ether | 1.0 | Ethanol | 1.0 |
| Preparation method 41 of Crystalline Form B | 40 | 15 | Acetonitrile | 1.0 | Toluene | 1.0 |
| Preparation method 42 of Crystalline Form B | 40 | 15 | Ethanol | 0.5 | Butanone | 1.5 |
| Preparation method 43 of Crystalline Form B | 40 | 15 | Isopropyl ether | 1.0 | Toluene | 1.0 |

The Sixth Experiment Method

About 10 mg of Crystalline form A was added to the corresponding solvent wherein, Acetone:Water=3:1 (volume ratio), Acetonitrile:Water=3:2 (volume ratio) to get a clear solution by ultrasonic, followed by filtration, to which was added 1 mg of polymer. The mixture was exposed to room temperature for volatilization to get the Crystalline form B.

| No. | Temperature (° C.) | Crystalline form A weight (mg) | Solvent | Solvent (Volume, mL) | Polymer |
|---|---|---|---|---|---|
| Preparation method 44 of Crystalline Form B | Room temperature | 10 | Methanol | 0.5 | Hydroxypropyl cellulose |

| No. | Temperature (° C.) | Crystalline form A weight (mg) | Solvent | Solvent (Volume, mL) | Polymer |
|---|---|---|---|---|---|
| Preparation method 45 of Crystalline Form B | Room temperature | 10 | Methanol | 0.5 | Ethyl cellulose |
| Preparation method 46 of Crystalline Form B | Room temperature | 10 | Acetone-Water | 0.4 | Hydroxypropyl cellulose |
| Preparation method 47 of Crystalline Form B | Room temperature | 10 | Acetone-Water | 0.4 | Ethyl cellulose |
| Preparation method 48 of Crystalline Form B | Room temperature | 10 | Acetone-Water | 0.4 | Povidone K30 |
| Preparation method 49 of Crystalline Form B | Room temperature | 10 | Acetone-Water | 0.4 | Polyallylamine hydrochloride |
| Preparation method 50 of Crystalline Form B | Room temperature | 10 | Acetone-Water | 0.4 | Carboxymethyl cellulose |
| Preparation method 51 of Crystalline Form B | Room temperature | 10 | Acetone-Water | 0.4 | Polyvinyl alcohol |
| Preparation method 52 of Crystalline Form B | Room temperature | 10 | Acetonitrile-Water | 0.5 | Hydroxypropyl cellulose |
| Preparation method 53 of Crystalline Form B | Room temperature | 10 | Acetonitrile-Water | 0.5 | Ethyl cellulose |
| Preparation method 54 of Crystalline Form B | Room temperature | 10 | Acetonitrile-Water | 0.5 | Povidone K30 |
| Preparation method 55 of Crystalline Form B | Room temperature | 10 | Acetonitrile-Water | 0.5 | Polyallylamine hydrochloride |
| Preparation method 56 of Crystalline Form B | Room temperature | 10 | Acetonitrile-Water | 0.5 | Carboxymethyl cellulose |
| Preparation method 57 of Crystalline Form B | Room temperature | 10 | Acetonitrile-Water | 0.5 | Polyvinyl alcohol |

The Seventh Experiment Method

About 15 to 50 mg of Crystalline form A was dissolved into corresponding solvent at corresponding temperature to get a clear solution, followed by filtration, the filtrate was placed at 4° C. being kept stirring until solid being observed and filtered to obtain the Crystalline form B. Among them, crystalline form not being observed into isopropanol at 4° C. with stirring, and then exposed to room temperature for volatilization to get the Crystalline form B.

| No. | Temperature (° C.) | The weight of Crystalline form A (mg) | Solvent | Solvent (Volume, mL) |
|---|---|---|---|---|
| Preparation method 58 of Crystalline Form B | 60 | 50 | Methanol | 1.0 |
| Preparation method 59 of Crystalline Form B | 70 | 15 | Ethanol | 1.2 |
| Preparation method 60 of Crystalline Form B | 70 | 15 | n-Propanol | 1.4 |
| Preparation method 61 of Crystalline Form B | 70 | 10 | n-Butanol | 2.0 |
| Preparation method 62 of Crystalline Form B | 70 | 50 | Water | 0.4 |
| Preparation method 63 of Crystalline Form B | 70 | 10 | Isopropanol | 2.0 |

The Eighth Experiment Method

About 10 to 15 mg of Crystalline form A was added to Solvent 2 first, then added to Solvent 1 to get a clear solution at the corresponding temperature, followed by filtration, then the filtrate was stirred at −20° C. until solid being observed, recovering the Crystalline form B. Among them, crystalline form not being observed with stirring using preparation method 69 to 74 of Crystalline form B, the filtrate was exposed to room temperature for volatilization to get the Crystalline form B.

| No. | Temperature (° C.) | The weight of Crystalline form A (mg) | Solvent 1 | Solvent 1 (Volume, mL) | Solvent 2 | Solvent 2 (Volume, mL) |
|---|---|---|---|---|---|---|
| Preparation method 64 of Crystalline Form B | 55 | 15 | Trifluoroethanol | 0.1 | Acetone | 0.3 |
| Preparation method 65 of Crystalline Form B | 55 | 15 | Water | 0.2 | Acetone | 1.0 |
| Preparation method 66 of Crystalline Form B | 70 | 15 | Water | 0.3 | Dioxane | 2.0 |
| Preparation method 67 of Crystalline Form B | 70 | 15 | Water | 0.3 | Acetonitrile | 3.0 |
| Preparation method 68 of Crystalline Form B | 55 | 10 | n-Propanol | 0.8 | Methyl tert-butyl ether | 0.7 |
| Preparation method 69 of Crystalline Form B | 60 | 15 | Methanol | 0.2 | Nitromethane | 1.0 |
| Preparation method 70 of Crystalline Form B | 60 | 15 | Methanol | 0.3 | Acetonitrile | 0.5 |
| Preparation method 71 of Crystalline Form B | 70 | 10 | Ethanol | 1.0 | Butanone | 0.5 |
| Preparation method 72 of Crystalline Form B | 70 | 10 | Ethanol | 1.6 | Ethyl acetate | 0.5 |
| Preparation method 73 of Crystalline Form B | 70 | 10 | Ethanol | 1.0 | 1,4-dioxane | 0.5 |
| Preparation method 74 of Crystalline Form B | 70 | 15 | Water | 0.3 | Tetrahydrofuran | 2.0 |

The Ninth Experiment Method

About 10 to 15 mg of Crystalline form A was added to solvent 1 to get a clear solution by ultrasonic at room temperature, then filtered, and added to solvent 2 dropwise with stirring until a large amount of solid being observed, and filtered to obtain the Crystalline form B. Among them, no solid being observed using the preparation methods 89 and 90 of Crystalline form B, then the mixture was exposed to room temperature for volatilization to get the Crystalline form B.

| No. | Sample weight (mg) | Solvent 1 | Solvent 1 (Volume, mL) | Solvent 2 | Solvent 2 (Volume, mL) |
|---|---|---|---|---|---|
| Preparation method 75 of Crystalline Form B | 15 | Methanol | 0.4 | Acetone | 5.0 |
| Preparation method 76 of Crystalline Form B | 15 | Methanol | 0.4 | Ethylacetate | 3.6 |
| Preparation method 77 of Crystalline Form B | 15 | Methanol | 0.4 | Methyl tert-butyl ether | 1.6 |
| Preparation method 78 of Crystalline Form B | 10 | Ethanol | 0.8 | Isopropyl ether | 3.0 |
| Preparation method 79 of Crystalline Form B | 10 | Ethanol | 0.8 | Isopropyl acetate | 5.0 |
| Preparation method 80 of Crystalline Form B | 15 | Trifluoroethanol | 0.2 | Acetone | 5.0 |
| Preparation method 81 of Crystalline Form B | 15 | Water | 0.4 | Acetone | 13.0 |
| Preparation method 82 of Crystalline Form B | 15 | Water | 0.4 | Tetrahydrofuran | 12.0 |
| Preparation method 83 of Crystalline Form B | 15 | Water | 0.4 | 1,4-dioxane | 13.0 |

-continued

| No. | Sample weight (mg) | Solvent 1 | Solvent 1 (Volume, mL) | Solvent 2 | Solvent 2 (Volume, mL) |
|---|---|---|---|---|---|
| Preparation method 84 of Crystalline Form B | 15 | Water | 0.4 | Acetonitrile | 5.0 |
| Preparation method 85 of Crystalline Form B | 10 | n-Propanol | 0.8 | Isopropyl acetate | 5.0 |
| Preparation method 86 of Crystalline Form B | 10 | n-Propanol | 0.8 | n-Heptane | 12.0 |
| Preparation method 87 of Crystalline Form B | 15 | Dimethyl sulfoxide | 0.2 | Dichloromethane | 5.0 |
| Preparation method 88 of Crystalline Form B | 15 | Methanol | 0.2 | Chloroform | 5.0 |
| Preparation method 89 of Crystalline Form B | 15 | Methanol | 0.4 | Dichloromethane | 5.0 |
| Preparation method 90 of Crystalline Form B | 10 | Ethanol | 0.8 | Tetrahydrofuran | 5.0 |

The Tenth Experiment Method

About 10 mg of amorphous sample of the compound of formula I was placed in a 2.0 mL of centrifuge tube. The centrifuge tube was then placed in the corresponding solvent atmosphere at room temperature for 6 days to obtain the Crystalline form B.

| No. | Sample weight (mg) | Solvent | Solvent (Volume, mL) |
|---|---|---|---|
| Preparation method 91 of Crystalline Form B | 10 | n-Butanol | 4.0 |
| Preparation method 92 of Crystalline Form B | 10 | Water | 4.0 |
| Preparation method 93 of Crystalline Form B | 10 | Nitromethane | 4.0 |
| Preparation method 94 of Crystalline Form B | 10 | Ethyl acetate | 4.0 |
| Preparation method 95 of Crystalline Form B | 10 | Methyl tert-butyl ether | 4.0 |
| Preparation method 96 of Crystalline Form B | 10 | Tetrahydrofuran | 4.0 |
| Preparation method 97 of Crystalline Form B | 10 | Dichloromethane | 4.0 |
| Preparation method 98 of Crystalline Form B | 10 | Chloroform | 4.0 |
| Preparation method 99 of Crystalline Form B | 10 | Toluene | 4.0 |

The Eleventh Experiment Method

About 15 to 30 mg of amorphous sample of the compound of formula I was added to the corresponding solvent at the corresponding temperature, and stirred for 30 minutes, followed by filtration to obtain the Crystalline Form B.

| No. | Temperature (° C.) | Sample weight (mg) | Solvent | Solvent (Volume, mL) |
|---|---|---|---|---|
| Preparation method 100 of Crystalline Form B | 4 | 15 | n-Propanol | 0.2 |
| Preparation method 101 of Crystalline Form B | 4 | 30 | Water | 0.1 |
| Preparation method 102 of Crystalline Form B | 4 | 10 | Butanone | 0.4 |
| Preparation method 103 of Crystalline Form B | 4 | 10 | Ethyl acetate | 0.4 |
| Preparation method 104 of Crystalline Form B | 4 | 10 | Tetrahydrofuran | 0.4 |
| Preparation method 105 of Crystalline Form B | 4 | 10 | Dichloromethane | 0.4 |
| Preparation method 106 of Crystalline Form B | Room temperature | 15 | Ethanol | 0.2 |
| Preparation method 107 of Crystalline Form B | Room temperature | 15 | Isopropanol | 0.2 |
| Preparation method 108 of Crystalline Form B | Room temperature | 15 | n-Butanol | 0.2 |
| Preparation method 109 of Crystalline Form B | Room temperature | 30 | Water | 0.1 |
| Preparation method 110 of Crystalline Form B | Room temperature | 10 | Acetone | 0.4 |
| Preparation method 111 of Crystalline Form B | Room temperature | 10 | Ether | 0.4 |
| Preparation method 112 of Crystalline Form B | Room temperature | 10 | Isopropyl acetate | 0.4 |
| Preparation method 113 of Crystalline Form B8 | Room temperature | 10 | 1,4-dioxane | 0.4 |
| Preparation method 114 of Crystalline Form B | Room temperature | 10 | Acetonitrile | 0.4 |

-continued

| No. | Temperature (° C.) | Sample weight (mg) | Solvent | Solvent (Volume, mL) |
|---|---|---|---|---|
| Preparation method 115 of Crystalline Form B | Room temperature | 10 | Chloroform | 0.4 |
| Preparation method 116 of Crystalline Form B | 40 | 10 | Sec-butanol | 0.4 |
| Preparation method 117 of Crystalline Form B | 40 | 10 | Nitromethane | 0.4 |
| Preparation method 118 of Crystalline Form B | 40 | 10 | Ethyl acetate | 0.4 |
| Preparation method 119 of Crystalline Form B | 40 | 10 | Tetrahydrofuran | 0.4 |
| Preparation method 120 of Crystalline Form B | 40 | 10 | Acetonitrile | 0.4 |
| Preparation method 121 of Crystalline Form B | 40 | 10 | Toluene | 0.4 |

The Twelfth Experiment Method

About 15 to 30 mg of amorphous sample of the compound of formula I was added to solvent 2 first, and then added to solvent 1 to get a suspension, stirred for 30 minutes at the corresponding temperature, filtered to obtain the Crystalline Form B.

| No. | Temperature (° C.) | Sample weight (mg) | Solvent 1 | Solvent 1 (Volume, mL) | Solvent 2 | Solvent 2 (Volume, mL) |
|---|---|---|---|---|---|---|
| Preparation method 122 of Crystalline Form B | Room temperature | 15 | Methanol | 0.2 | Isopropyl ether | 0.6 |
| Preparation method 123 of Crystalline Form B | 40 | 15 | Methanol | 0.1 | Ethyl acetate | 0.6 |
| Preparation method 124 of Crystalline Form B | 4 | 15 | Methanol | 0.05 | 1,4-dioxane | 1.0 |
| Preparation method 125 of Crystalline Form B | 4 | 10 | Ethanol | 0.1 | Butanone | 1.0 |
| Preparation method 126 of Crystalline Form B | Room temperature | 10 | Ethanol | 0.2 | Acetonitrile | 3.0 |
| Preparation method 127 of Crystalline Form B | 40 | 10 | Ethanol | 0.2 | n-Heptane | 0.8 |
| Preparation method 128 of Crystalline Form B | Room temperature | 15 | Trifluoro ethanol | 0.05 | Nitromethane | 0.6 |
| Preparation method 129 of Crystalline Form B | 4 | 15 | Trifluoro ethanol | 0.1 | Ether | 0.8 |
| Preparation method 130 of Crystalline Form B | 40 | 15 | Trifluoro ethanol | 0.05 | Tetrahydrofuran | 0.8 |
| Preparation method 131 of Crystalline Form B | Room temperature | 15 | Water | 0.05 | Acetone | 1.0 |
| Preparation method 132 of Crystalline Form B | 4 | 15 | Water | 0.05 | Tetrahydrofuran | 1.0 |
| Preparation method 133 of Crystalline Form B | Room temperature | 15 | Water | 0.05 | Acetonitrile | 1.0 |
| Preparation method 134 of Crystalline Form B | Room temperature | 10 | Isopropanol | 0.2 | Methyl tert-butyl ether | 0.6 |
| Preparation method 135 of Crystalline Form B | 4 | 10 | n-Propanol | 0.2 | Isopropyl acetate | 0.6 |
| Preparation method 136 of Crystalline Form B | 40 | 10 | n-Butanol | 0.2 | Methyl cyclohexane | 0.8 |
| Preparation method 137 of Crystalline Form B | 4 | 15 | Dimethyl sulfoxide | 0.1 | Acetone | 1.6 |
| Preparation method 138 of Crystalline Form B | 40 | 15 | Dimethyl sulfoxide | 0.05 | Ethyl acetate | 1.0 |

-continued

| No. | Temperature (° C.) | Sample weight (mg) | Solvent 1 | Solvent 1 (Volume, mL) | Solvent 2 | Solvent 2 (Volume, mL) |
|---|---|---|---|---|---|---|
| Preparation method 139 of Crystalline Form B | Room temperature | 15 | Dimethyl sulfoxide | 0.05 | Acetonitrile | 1.0 |
| Preparation method 140 of Crystalline Form B | Room temperature | 10 | Chloroform | 0.4 | Methyl tert-butyl ether | 0.4 |
| Preparation method 141 of Crystalline Form B | Room temperature | 10 | Ethyl acetate | 0.4 | Toluene | 0.4 |

The Thirteenth Experiment Method Preparation Method 142 of Crystalline Form B

About 10 mg of amorphous sample of the compound of formula I was placed in an atmosphere of 85% RH humidity for 10 days at room temperature to obtain the Crystalline form B.

The Fourteenth Experiment Method

The appropriate amount of sample was added to the corresponding solvent, to get a clear solution by ultrasonic, followed by filtration, then the filtrate was spin-dried rapidly at the corresponding water bath temperature to obtain the Crystalline form B.

| No. | Temperature (° C.) | Sample weight (mg) | Solvent | Solvent 1 (Volume, mL) |
|---|---|---|---|---|
| Preparation method 143 of Crystalline Form B | 60 | 15 | Water | 0.4 |
| Preparation method 144 of Crystalline Form B | 40 | 1000 | Methanol | 40.0 |

Example 4: Preparation Method of Crystalline form C

Preparation Method 1 of Crystalline Form C:

100 mg of Crystalline form A of the compound of formula I was added to 2.8 mL of isopropyl ether, followed by added to 2.8 mL of methanol to form a suspension. The mixture was stirred for 4 days at room temperature and filtered in vacuum to obtain 73 mg of the Crystalline form C.

Preparation Method 2 of Crystalline Form C:

100 mg of Crystalline form A of the compound of formula I was added to 1.0 mL of isopropyl ether, followed by added to 3.0 mL of methanol to form a suspension. The mixture was stirred at room temperature for 5 days and filtered in vacuum to obtain 63 mg of the Crystalline form C.

Preparation method 3 and 4 of Crystalline form C:

About 15 mg of Crystalline Form A of the compound of formula I was dissolved into solvent 2, followed by dissolved into solvent 1 to get a clear solution, filtered and stirred at −20° C. until solid being observed, recovering the Crystalline Form C.

| No. | Temperature (° C.) | Sample weight (mg) | Solvent 1 | Solvent 1 (mL) | Solvent 2 | Solvent 2 (mL) |
|---|---|---|---|---|---|---|
| Preparation method 3 | 60 | 15 | Methanol | 1.1 | Isopropyl ether | 0.5 |
| Preparation method 4 | 60 | 15 | Methanol | 0.6 | Isopropyl acetate | 0.5 |

Preparation Method 5 of Crystalline Form C:

About 10 mg of Crystalline Form A of the compound of formula I was placed in a 2.0 mL of centrifuge tube, and exposed to 4 mL of methanol closed solvent atmosphere for 6 days at room temperature to obtain the Crystalline form C.

Example 5: Preparation Method of Crystalline Form D

Preparation Method 1 of Crystalline form D:

100 mg of Crystalline form A of the compound of formula I was added to 2.0 mL of ethyl acetate, then added to 1.0 mL of dimethyl sulfoxide to form a suspension. The suspension was stirred at room temperature for 1 day to obtain the Crystalline form D.

Preparation Method 2 of Crystalline form D:

About 5 mg of Crystalline form A of the compound of formula I was dissolved into 0.1 mL of dimethylsulfoxide to get a clear solution, followed by filtration, and exposed to 40° C. for volatilization to get the Crystalline form.

Preparation Method 3 of Crystalline Form D:

About 20 mg of Crystalline form A of the compound of formula I was added to solvent 2, then added to solvent 1 to form a suspension. The mixture was stirred at the corresponding temperature for 4 days to obtain the Crystalline form D.

| Temperature (° C.) | Sample weight (mg) | Solvent 1 | Solvent 1 (mL) | Solvent 2 | Solvent 2 (mL) |
|---|---|---|---|---|---|
| 40 | 20 | Ethyl acetate | 1.0 | Dimethyl sulfoxide | 0.5 |

Preparation Method 4 and 5 of Crystalline Form D:

About 15 mg of Crystalline form A of the compound of formula I was added to solvent 1 to get a clear solution by ultrasonic at room temperature, followed by filtration, and then the solvent 2 was added dropwise to the solution with stirring until a large amount of solid being observed, recovering the Crystalline form D.

| No. | Sample weight (mg) | Solvent 1 | Solvent 1 (mL) | Solvent 2 | Solvent 2 (mL) |
|---|---|---|---|---|---|
| preparation method 4 | 15 | Dimethyl sulfoxide | 0.2 | Acetone | 3.0 |
| preparation method 5 | 15 | Dimethyl sulfoxide | 0.2 | Ethyl acetate | 5.0 |

Example 6: Preparation Method of Crystalline Form E

About 20 mg of Crystalline form A of the compound of formula I was placed in 85% RH Humidity Apparatus for 26 days at room temperature to get the Crystalline form E.

| No. | Temperature (° C.) | Sample weight (mg) | Solvent | Solvent (mL) |
|---|---|---|---|---|
| Preparation method 3 | Room temperature | 5 | Trifluoroethanol | 0.4 |
| Preparation method 4 | 40 | 5 | n-Propanol | 1.0 |
| Preparation method 5 | 40 | 10 | Trifluoroethanol | 0.4 |

Preparation Method 6-9 of Amorphis:

About 10 mg of Crystalline form A of the compound of formula I was dissolved into the corresponding solvent to get a clear solution, followed by filtration, and exposed to the corresponding temperature for volatilization to obtain the amorphis.

| No. | Temperature (° C.) | Sample weight (mg) | Solvent 1 | Solvent 1 (mL) | Solvent 2 | Solvent 2 (mL) |
|---|---|---|---|---|---|---|
| Preparation method 6 | Room temperature | 10 | Trifluoro-ethanol | 0.2 | Acetonitrile | 0.2 |
| Preparation method 7 | 60 | 10 | n-Propanol | 1.0 | Toluene | 0.4 |
| Preparation method 8 | 60 | 10 | Sec-butanol | 2.0 | 1,4-dioxane | 0.4 |
| Preparation method 9 | 60 | 10 | n-Butanol | 2.0 | n-Heptane | 0.6 |

Example 7: Preparation Method of Amorphis

Preparation Method 1 of Amorphis:

200 mg of Crystalline form A of the compound of formula I was added to 0.6 mL of trifluoroethanol to get a clear solution by ultrasonic, followed by filtration, and the filtrate was spin-dried rapidly in vacuum at 40° C. to obtain the amorphis.

Preparation Method 2 of Amorphis:

200 mg of Crystalline form A of the compound of formula I was added to 7.0 mL of methanol to get a clear solution by ultrasonic, followed by filtration, and spin-dried rapidly in vacuum at 40° C. to obtain the amorphis.

Preparation Method 3-5 of Amorphis:

5 to 10 mg of Crystalline form A of the compound of formula I was dissolved into the corresponding solvent to get a clear solution, followed by filtration, and exposed to the corresponding temperature for volatilization to obtain the amorphis.

Preparation Method 10 of Amorphis:

About 15 mg of Crystalline form A of the compound of formula I was added to 2.0 mL of n-heptane, the mixture was stirred at room temperature for 5 days to obtain the amorphis.

Preparation Method 11-12 of Amorphis:

About 10 to 15 mg of Crystalline form A of the compound of formula I was dissolved into the corresponding solvent to get a clear solution at the corresponding temperature, followed by filtration, and stirred at −20° C. until solid being observed, recovering the amorphis.

| No. | Temperature (° C.) | Sample weight (mg) | Solvent 1 | Solvent 1 (mL) | Solvent 2 | Solvent 2 (mL) |
|---|---|---|---|---|---|---|
| Preparation method 11 | 70 | 15 | Trifluoroethanol | 0.1 | Acetonitrile | 2.0 |
| Preparation method 12 | 70 | 10 | Sec-butanol | 2.0 | n-Heptane | 0.8 |

Preparation Method 13 of Amorphis:

About 15 mg of Crystalline form A of the compound of formula I was added to 0.2 mL of trifluoroethanol to get a clear solution by ultrasonic at room temperature, followed by filtration, 1.0 mL of isopropyl ether was added dropwise to the solution with stirring until a large amount of solid being observed, recovering the amorphis.

Preparation Method 14-17 of Amorphis:

About 10 to 15 mg of Crystalline form A of the compound of formula I was dissolved into the corresponding solvent to get a clear solution, followed by filtration, and the filtrate was spin-dried rapidly at the corresponding temperature to obtain the amorphis.

| No. | Temperature (° C.) | Sample weight (mg) | Solvent 1 | Solvent 1 (mL) | Solvent 2 | Solvent 2 (mL) |
|---|---|---|---|---|---|---|
| Preparation method 14 | 40 | 10 | Ethanol | 1.0 | NA | NA |
| Preparation method 15 | 40 | 15 | Methanol | 0.4 | Dichloromethane | 0.4 |
| Preparation method 16 | 40 | 10 | Ethanol | 1.5 | Chloroform | 0.5 |
| Preparation method 17 | 40 | 15 | Trifluoro-ethanol | 0.2 | Acetonitrile | 0.4 |

Example 8: Stability of the Crystalline Form

Samples of Crystalline form A and B were placed at 80° C. for 24 hours, 25° C.-60% RH for 10 days and 40° C.-75% RH for 10 days respectively, there were no change in crystalline form.

Crystalline form C was almost completely converted to Crystalline form A under the condition of being dried in vacuum at room temperature overnight.

Most of the Crystalline form D transformed into Crystalline form B under conditions of being dried at room temperature or being dried in vacuum at room temperature, which can not exist stably.

Most of the Crystalline form E transformed into Crystalline form A. under the condition of being placed in a desiccator for 2 days, which is unstable.

Example 9: Assay of Dynamic Vapor Sorption (DVS)

Crystalline form A: There was about 2.3% weight change in the range of 0% to 80% RH. The hydrate of Crystalline form A removed about 1.5% of moisture in the 0% RH drying stage, and absorbed about 2.3% of moisture in the 0% RH-80% RH range. In the desorption stage, 1.5% of moisture could be removed under the condition of 30% RH and the change of the weight was less than 2% in the range of 30-80% RH.

Crystalline form B: There was about 2.3% weight change in the range of 0% to 80% RH. The hydrate of Crystalline form B could remove about 4% of moisture under 10% RH, and absorbed about 4% of moisture under the condition of 10% RH in the adsorption stage and the change of weight was less than 2% in the range of 10-80% RH.

Amorphis: There was about 15.7% weight change in the range of 0-80% RH, extremely hygroscopic.

Example 10: Solubility Determination

The solubility of Crystalline form A of the compound as shown in formula I in water is 20 to 100 mg/mL at room temperature, and the solubility of the free base amorphis of the compound as shown in formula I in water is less than 1 mg/mL.

Example 11. Capsule Formulation

As an explicit embodiment of an oral medication, about 20 to 150 mg of the polymorphs described in example 1 and/or example 2 are formulated with finely divided microcrystalline cellulose and/or stearic acid to obtain a total amount of about 50 mg to 500 mg to fill 0 type capsule.

Example 12. Formulation of Tablets or Capsules

As an explicit embodiment of an oral medication, about 20 to 150 mg of the polymorphs described in example 1 and/or example 2 are formulated with the two or more of the following excipient: finely divided microcrystalline cellulose, mannitol, crospovidone, croscarmellose sodium, sodium starch glycolate, povidone, hydroxypropylcellulose and/or stearic acid to allocate a total amount of about 50 mg to 500 mg of tablet or capsule.

Example 13: Pharmacokinetic Data 6 female SD rats were divided into two groups, three rats in each group. 50 mg/kg of Crystalline form A of the compound of formula I and free base amorphis of the compound of formula I were administered by intragastric gavage at single dose to each female SD rat respectively; the blood samples were collected through the jugular vein at the specified time, and the plasma from these samples was separated and stored in the refrigerator at −80° C.

For the above plasma from these samples, protein was precipitated using acetonitrile, the supernatant was diluted 3-fold by water, then took 5 μL of the solution for LC-MS/MS test, and data is shown in Table 9:

TABLE 9

| Compound | Administration methods | Dose (mg/kg) | $T_{max}$ (h) | $C_{max}$ (ng/mL) | $AUC_{last}$ (h*ng/mL) |
|---|---|---|---|---|---|
| Free base amorphous of the compound as shown in formula I | PO | 50 | 4.67 | 890 | 8165 |
| Crystalline form A of the compound as shown in formula I | PO | 50 | 2.67 | 1440 | 11551 |

50 mg/kg of Crystalline form A of the compound as shown in formula I and free base amorpphis of the compound as shown in formula I were administered orally to the rats, $T_{max}$ were 2.67 and 4.67 h respectively, $C_{max}$ were 1440 and 890 ng/mL respectively, and $AUC_{last}$ were 11551 and 8165 h*ng/mL, respectively.

From the above results, it is suggested that Crystalline form A of the compound as shown in formula I showed higher absorption in vivo than the free base amorphis of the compound as shown in formula I.

Example 14: Biochemical Kinase Activity of the Compound of Formula I

Biochemical kinase activity of the compound as shown in formula I was tested by Reaction Biology Corp located in Malvern, Pa., USA. The testing rules is described in *Nat Biotechnol.* 2011; 29(11):1039-45 by Anastassiadis et al. It was found that the compound of Formula I could potentially inhibit the following kinases:

| Kinase | IC$_{50}$ (nM) |
|---|---|
| ALK | 0.16 |
| ALK (C1156Y) | 0.28 |
| ALK (F1174L) | 0.16 |
| ALK (Fl 174L)-EML4 | 0.53 |
| ALK (Fl 174L)-NPM1 | 0.47 |
| ALK (F1174S) | 0.17 |
| ALK (G1202R) | 3.83 |
| ALK (G1269A) | 1.14 |
| ALK (G1269S) | 1.39 |
| ALK(L1152R) | 0.58 |
| ALK(L1196M) | 0.32 |
| ALK (R1275Q) | 1.06 |
| ALK (S1206R) | 0.17 |
| ALK (T1151-L1152insT) | 0.26 |
| ALK (T1151M) | 0.13 |
| ALK-NPM1 | 0.68 |
| c-MET | 9.59 |
| EPHA1 | 6.22 |
| EPHA2 | 1.14 |
| EPHB1 | 8.59 |
| CSF1R (FMS) | 13.44 |
| NEK1 | 6.08 |
| ROS/ROS1 | 1.41 |
| ROS1-GOPC | 0.98 |
| TRKA | 8.00 |
| TRKA-TFG (TRK-T3) | 0.46 |
| TRKA-TPM3 | 0.62 |
| TRKA-TPR | 1.22 |
| TRKB | 3.39 |
| TRKC | 0.46 |
| ALK-TFG | 0.73 |
| ALK-TPM3 | 0.21 |

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention.

The invention claimed is:

1. A crystalline form of a compound of formula I, hydrates and/or solvates thereof Formula I

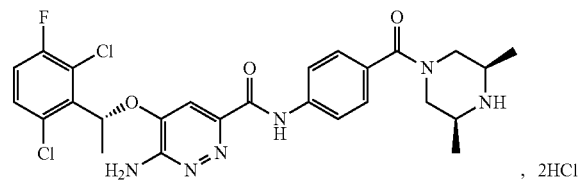

, 2HCl wherein an X-ray powder diffraction pattern of the crystalline form has characteristic peaks at diffraction angles 2θ of 4.9±0.2°, 10.0±0.2° and 19.3±0.2°.

2. The crystalline form of the compound of formula I, hydrates and/or solvates thereof according to claim 1, wherein the X-ray powder diffraction pattern of the crystalline form has characteristic peaks at diffraction angles 2θ of 4.9±0.2°, 10.0±0.2°, 14.7±0.2°, 16.9±0.2°, 19.3±0.2° and 20.3±0.2°.

3. The crystalline form of the compound of formula I, hydrates and/or solvates thereof according to claim 1, wherein the X-ray powder diffraction pattern of the crystalline form has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2°.

Figure 1:
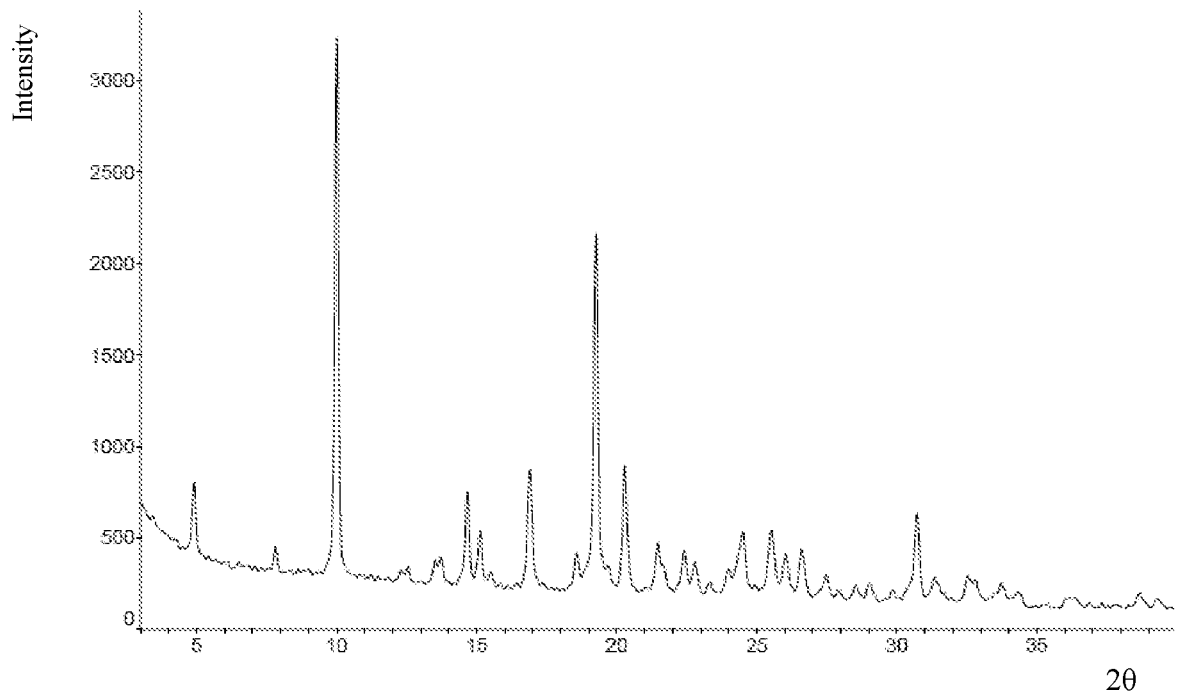
FIG. 1: The X-ray powder diffraction pattern of Crystalline form A of the compound as shown in formula I.

4. The crystalline form of the compound of formula I, hydrates and/or solvates thereof according to claim 1, wherein the crystalline form has the X-ray powder diffraction pattern approximately as shown in FIG. 1.

5. The crystalline form of the compound of formula I, hydrates and/or solvates thereof according to claim 1, wherein the crystalline form is a dihydrate.

6. A crystalline form of a compound of formula I, hydrates and/or solvates thereof Formula I

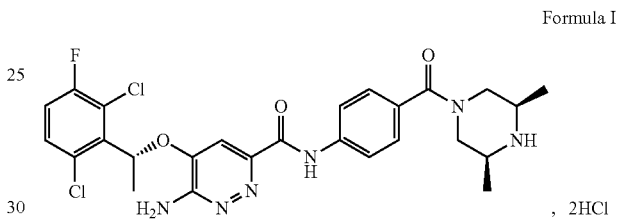

, 2HCl wherein an X-ray powder diffraction pattern of the crystalline form has characteristic peaks at diffraction angles 2θ of 10.5±0.2°, 17.4±0.2° and 21.1±0.2°.

7. The crystalline form of the compound of formula I, hydrates and/or solvates thereof according to claim 6, wherein the X-ray powder diffraction pattern of the crystalline form has characteristic peaks at diffraction angles 2θ of 10.5±0.2°, 17.4±0.2°, 19.7±0.2°, 21.1±0.2°, 23.9±0.2° and 25.5±0.2°.

8. The crystalline form of the compound of formula I, hydrates and/or solvates thereof according to claim 6, wherein the X-ray powder diffraction pattern of the crystalline form has characteristic peaks at diffraction angles 2θ of 10.5±0.2°, 17.4±0.2°, 19.7±0.2°, 21.1±0.2°, 21.5±0.2°, 23.9±0.2°, 25.2±0.2° and 25.5±0.2°.

Figure 2:
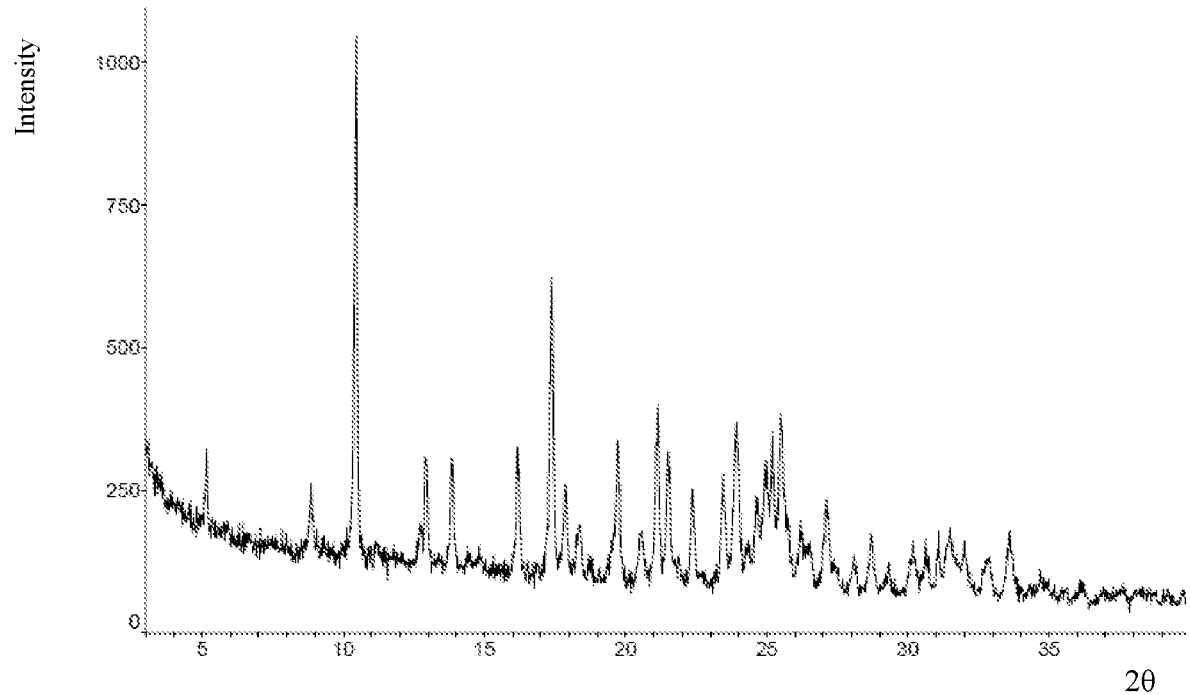
FIG. 2: The X-ray powder diffraction pattern of Crystalline form B of the compound as shown in formula I.
Figure 3:
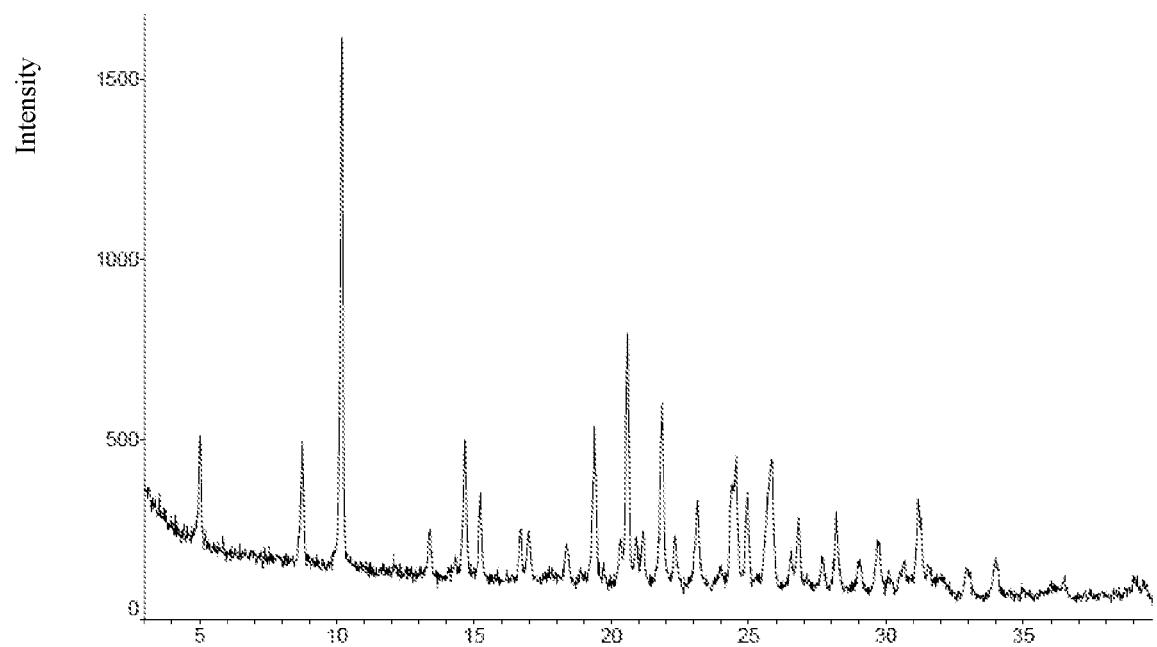
FIG. 3: The X-ray powder diffraction pattern of Crystalline form C of the compound as shown in formula I.
Figure 4:
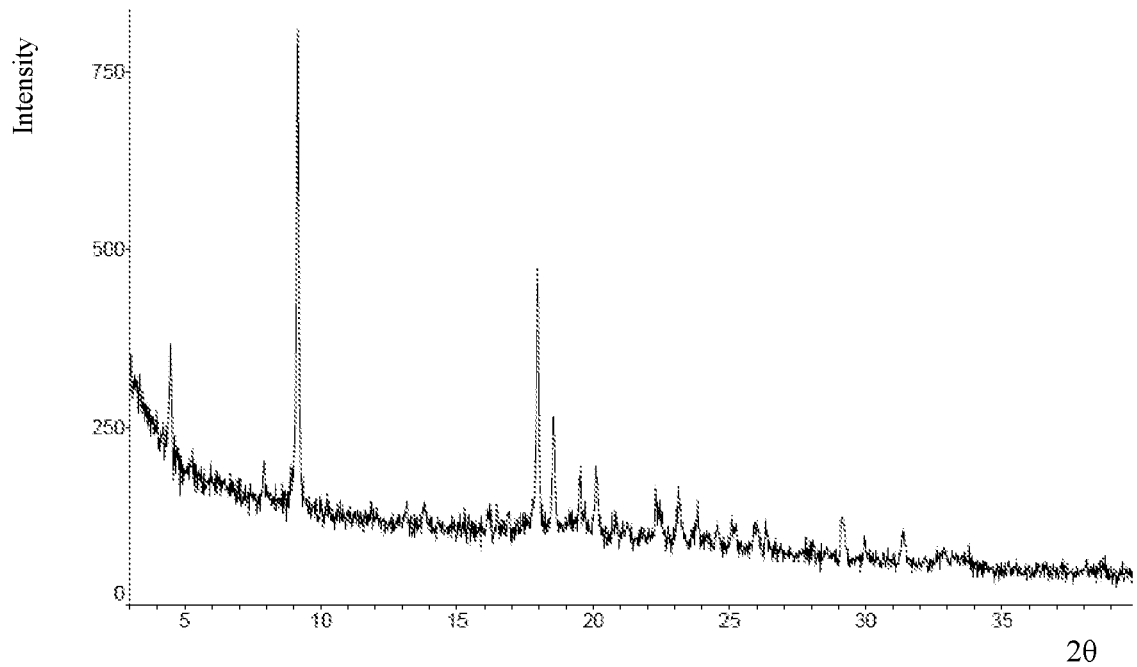
FIG. 4: The X-ray powder diffraction pattern of Crystalline form D of the compound as shown in formula I.
Figure 5:
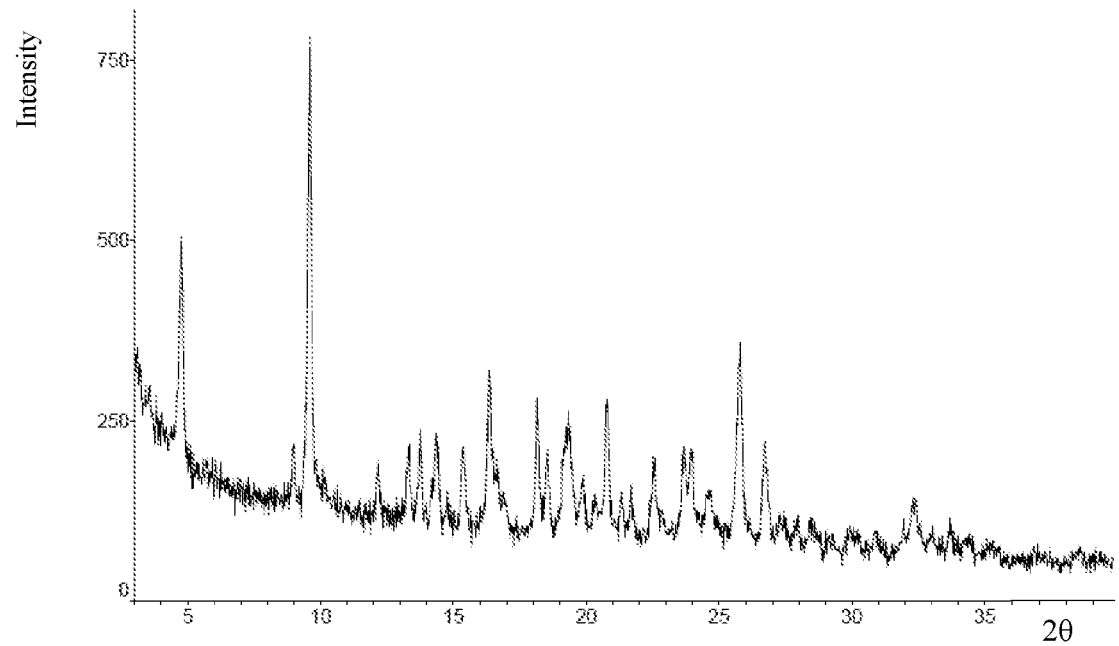
FIG. 5: The X-ray powder diffraction pattern of Crystalline form E of the compound as shown in formula I.
Figure 6:
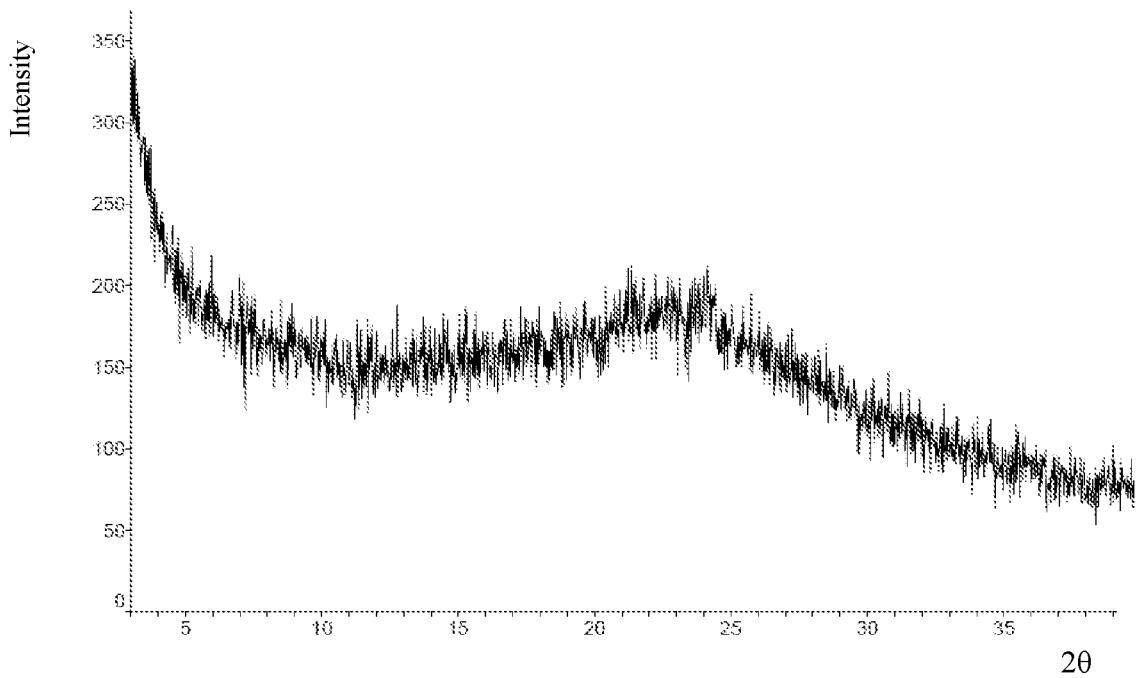
FIG. 6: The X-ray powder diffraction pattern of amorphous sample of the compound as shown in formula I.

9. The crystalline form of the compound of formula I, hydrates and/or solvates thereof according to claim 6, wherein the X-ray powder diffraction pattern approximately as shown in FIG. 2.

10. The crystalline form of the compound of formula I, hydrates and/or solvates thereof according to claim 6, wherein the crystalline form is a trihydrate.

11. The crystalline form of the compound of formula I, hydrates and/or solvates thereof according to claim 3, wherein the crystalline form has a purity of ≥85%.

12. The crystalline form of the compound of formula I, hydrates and/or solvates thereof according to claim 3, wherein the crystalline form has a purity of ≥95%.

13. The crystalline form of the compound of formula I, hydrates and/or solvates thereof according to claim 3, wherein the crystalline form has a purity of ≥99%.

14. A pharmaceutical composition, comprising a therapeutically effective amount of the crystalline form of the compound of formula I, hydrates and/or solvates thereof according to claim 3, and pharmaceutically acceptable excipients, adjuvants and/or carriers, and optionally at least one of other active ingredients.

15. The pharmaceutical composition according to claim 14, wherein the pharmaceutical composition is in a form of an oral preparation.

16. The pharmaceutical composition according to claim 14, wherein the pharmaceutical composition is in a form of a tablet or a capsule.

17. The pharmaceutical composition according to claim 14, wherein 20 mg to 150 mg of the crystalline form is formulated with at least one excipient, adjuvant and/or carrier to a total amount of about 50 mg to 500 mg.

18. The pharmaceutical composition according to claim 14, wherein the excipient, adjuvant and/or carrier is microcrystalline cellulose, mannitol, crospovidone, croscarmellose sodium cellulose, sodium starch glycolate, povidone, hydroxypropyl cellulose, and/or stearic acid.

19. The pharmaceutical composition according to claim 14, wherein the pharmaceutical composition comprises 0.01% to 99% by weight of the crystalline form.

20. The pharmaceutical composition according to claim 14, wherein the pharmaceutical composition comprises 0.1% to 70% by weight of the crystalline form.

21. The pharmaceutical composition according to claim 14, wherein the pharmaceutical composition comprises 1% to 70% by weight of the crystalline form.

22. The pharmaceutical composition according to claim 14, wherein the pharmaceutical composition comprises 1% to 50% by weight of the crystalline form.

23. The pharmaceutical composition according to claim 14, wherein the pharmaceutical composition comprises 1% to 30% by weight of the crystalline form.

24. The pharmaceutical composition according to claim 14, wherein the pharmaceutical composition comprises 10% to 30% by weight of the crystalline form.

25. A method for treating a disease, disorder or condition in a patient, administering to a patient the crystalline form of the compound of formula I, hydrates and/or solvates thereof according to claim 3 or the pharmaceutical composition comprising a therapeutically effective amount of the crystalline form of the compound of formula I, hydrates and/or solvates thereof, and pharmaceutically acceptable excipients, adjuvants and/or carriers, and optionally at least one of other active ingredients, wherein the disease, disorder or condition in a patient is selected from lung cancer, melanoma, colon cancer, breast cancer, liver cancer, pancreatic cancer, brain cancer, kidney cancer, ovarian cancer, gastric cancer, skin cancer, bone cancer, glioma, lymphoma, neuroblastoma, hepatocellular carcinoma, papillary renal cell carcinoma, and/or head and neck squamous cell carcinoma.

26. The method for treating a disease, disorder or condition in a patient according to claim 25, wherein the disease, disorder or condition is non-small cell lung cancer resistant to crizotinib therapy.

27. The method for treating a disease, disorder or condition in a patient according to claim 25, wherein the disease, disorder or condition is melanoma.

28. The method for treating a disease, disorder or condition in a patient according to claim 25, wherein the disease, disorder or condition is neurological disease, psychiatric disease, obesity, diabetes, and/or cardiovascular disease.

29. The method for treating a disease, disorder or condition in a patient according to claim 28, wherein the psychotic disease is schizophrenia, depression, and/or addiction or abuse of substance.

30. The method for treating a disease, disorder or condition in a patient according to claim 29, wherein the addiction or abuse of substance is addiction or abuse of cocaine, tobacco or alcohol.

31. A method for preparing the crystalline form of the compound of formula I, hydrates and/or solvates thereof according to claim 3, comprising following steps:
an amorphous sample of the compound of formula I was placed in centrifuge tubes, and stored in an airtight ethanol or acetonitrile atmosphere for 6 to 10 days at room temperature to obtain the crystalline form; or
an amorphous sample of the compound of formula I was added into ethanol, stirred at 4 ° C. to 25 ° C., and filtrated to give the crystalline form; or
an amorphous sample of the compound of formula I was added into ethanol at 4 ° C. to 25 ° C., and dissolved to get a clear solution; the solution was filtered to give filtrate; then the filtrate was added with n-heptane under stirring until a large amount of crystal being observed, then filtered to obtain the crystalline form; or
an amorphous sample of the compound of formula I was added into methyl tert-butyl ether/ethanol or n-heptane/ethanol at 55 ° C. to 70 ° C., and dissolved to get a clear solution; and the solution was filtered to give filtrate; then the filtrate was stirred at -20 ° C. until solid being observed, and filtered to obtain the crystalline form; or
an amorphous sample of the compound of formula I was added into methanol, and dissolved to get a clear solution, filtrated, then exposed to 35 ° C. to 50 ° C. to evaporate solvent, giving the crystalline form; or
an amorphous sample of the compound of formula I was added into methanol, and dissolved to get a clear solution; the solution was filtered to give filtrate; then the filtrate was added with carboxymethyl cellulose, and exposed to room temperature to evaporate solvent, obtaining the crystalline form.

32. A method for preparing the crystalline form of the compound of formula I, hydrates and/or solvates thereof according to claim 8, comprising following steps:
the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into methanol, ethanol or water, dissolved to get a clear solution, filtered, then exposed to room temperature (20 ° C.) to 40 ° C. to evaporate solvent, obtaining the crystalline form; or
the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into methanol/water, methanol/acetone, methanol/ethyl acetate, methanol/methyl tert-butyl ether, methanol/tetrahydrofuran, methanol/dichloromethane, ethanol/water, ethanol/butanone, ethanol/isopropyl acetate, ethanol/n-heptane, trifluoroethanol/water, trifluoroethanol/ethyl acetate, trifluoroethanol/tetrahydrofuran, water/methanol, water/ethanol, water/trifluoroethanol, water/isopropanol, water/acetone, water/tetrahydrofuran, or water/acetonitrile, dissolved to get a clear solution; then the solution was filtrated and exposed to room temperature (20 ° C.) to 40 ° C. to evaporate solvent, obtaining the crystalline form; or
the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added to a lower alcohol, water, nitromethane, butanone, diethyl ether, ethyl acetate, tetrahydrofuran, toluene or n-heptane to form a suspension; then the suspension was stirred for 4 to 5 days at room temperature to 40 °C., and centrifuged to obtain the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added to water-saturated ethyl acetate layer, ethyl acetate saturated aqueous layer, ethanol/diethyl ether, toluene/acetonitrile, butanone/ethanol or toluene/isopropyl ether to form a suspension; then the suspension was stirred at 4 °C. to 40 °C. for 4 to 5 days and centrifuged to obtain the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into methanol, acetone/water (3:1 v/v), or acetonitrile/water (3:2 v/v) at room temperature, and dissolved to get a clear solution; then the solution were added with hydroxypropylcellulose, ethylcellulose, povidone K30, polyallylamine hydrochloride, carboxymethyl cellulose, or polyvinyl alcohol, exposed to room temperature to evaporate solvent, obtaining the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into a lower alcohol or water at 60 °C. to 70 °C., dissolved to get a clear solution, and stirred at 4 °C. until crystals being observed, obtaining the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into acetone/trifluoroethanol, acetone/water, dioxane/water, acetonitrile/water or methyl tert-butyl ether/n-propanol at 55 °C. to 70 °C., dissolved to get a clear solution; and the solution was filtered to give filtrate; then the filtrate was stirred at -20 °C. until crystal being observed, then filtered to give the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into nitromethane/methanol, acetonitrile/methanol, butanone/ethanol, ethyl acetate/ethanol, 1,4-dioxane/ethanol or tetrahydrofuran/water at 60 °C. to 70 °C., and dissolved to get a clear solution, filtered and exposed to room temperature to evaporate solvent, obtaining the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into methanol, ethanol, water, trifluoroethanol, n-propanol or dimethyl sulfoxide at room temperature, and dissolved to get a clear solution; the solution was filtered, and the filtrate was added dropwise with acetone, ethyl acetate, methyl tert-butyl ether, isopropyl ether, isopropyl acetate, tetrahydrofuran, 1,4-dioxane, acetonitrile, n-heptane, methylene chloride or chloroform until a large amount of crystal being observed, obtaining the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was added into methanol or ethanol at room temperature, and dissolved to get a clear solution; and the solution was then filtrated to give filtrate; then the filtrate was added with dichloromethane or tetrahydrofuran, and exposed to room temperature to evaporate solvent, obtaining the crystalline form; or an amorphous sample of the compound of formula I was placed in centrifuge tubes, and then the centrifuge tubes were placed in the atmosphere of n-butanol, water, nitromethane, ethyl acetate, methyl tert-butyl ether, tetrahydrofuran, dichloromethane, chloroform and toluene to diffuse, to give the crystalline form; or an amorphous sample of the compound of formula I was added to n-propanol, water, butanone, ethyl acetate, tetrahydrofuran, dichloromethane, ethanol, isopropanol, n-butanol, acetone, ester, isopropyl acetate, 1,4-dioxane, acetonitrile, chloroform, sec-butanol, nitromethane or toluene, stirred at -4 °C. to -40 °C. for 30 minutes, then filtered to give the crystalline form; or an amorphous sample of the compound of formula I was added into isopropyl ether/methanol, ethyl acetate/methanol, 1,4-dioxane/methanol, butanone/ethanol, acetonitrile/ethanol, n-heptane/trifluoroethanol, nitromethane/trifluoroethanol, ether/trifluoroethanol, tetrahydrofuran/trifluoroethanol, acetone/water, tetrahydrofuran/water, acetonitrile/water, methyl tert-butyl ether/isopropanol, isopropyl acetate/n-propanol, methylcyclohexane/n-butanol, acetone/dimethylsulfoxide, ethyl acetate/dimethyl sulfoxide, acetonitrile/dimethyl sulfoxide, methyl tert-butyl ether/chloroform, or toluene/ethyl acetate to form a suspension, stirred at 4 °C. to 40 °C., then filtered to give the crystalline form; or an amorphous sample of the compound of formula I was placed at room temperature at a humidity of 85% RH to obtain the crystalline form; or the crystalline form of the compound of formula I of which the X-ray powder diffraction pattern has characteristic peaks at diffraction angles 2θ of 4.9±0.2°, 10.0±0.2°, 14.7±0.2°, 16.9±0.2°, 19.3±0.2°, 20.3±0.2°, 25.5±0.2° and 30.7±0.2° was dissolved into water or methanol to get a clear solution; the solution was filtered to give filtrate; then the filtrate was rotary evaporated to dry, obtaining the crystalline form.

\* \* \* \* \*